US008304509B2

(12) United States Patent
Gürtler et al.

(10) Patent No.: US 8,304,509 B2
(45) Date of Patent: Nov. 6, 2012

(54) PROCESS FOR PREPARING DIARYL CARBONATES FROM DIALKYL CARBONATES

(75) Inventors: Christoph Gürtler, Köln (DE); Thomas Ernst Müller, München (DE); Pieter Ooms, Krefeld (DE); Friedhelm Risse, Köln (DE); Johann Rechner, Kempen (DE); Franco Doro, Aachen (DE); Angelina Prokofieva, Aachen (DE)

(73) Assignee: Bayer Intellectual Property GmbH, Monheim (DE)

(*) Notice: Subject to any disclaimer, the term of this patent is extended or adjusted under 35 U.S.C. 154(b) by 0 days.

(21) Appl. No.: 13/251,381

(22) Filed: Oct. 3, 2011

(65) Prior Publication Data
US 2012/0101247 A1   Apr. 26, 2012

(30) Foreign Application Priority Data

Oct. 8, 2010  (DE) .......................... 10 2010 042 215
Oct. 26, 2010 (DE) .......................... 10 2010 042 937

(51) Int. Cl.
C08G 64/06   (2006.01)
C08G 64/00   (2006.01)

(52) U.S. Cl. ...................................... 528/196; 528/198
(58) Field of Classification Search .................. 528/196, 528/198
See application file for complete search history.

(56) References Cited

U.S. PATENT DOCUMENTS

| | | | |
|---|---|---|---|
| 3,642,858 A | 2/1972 | Frevel et al. |
| 3,803,201 A | 4/1974 | Gilpin et al. |
| 4,062,884 A | 12/1977 | Romano et al. |
| 4,131,521 A | 12/1978 | Cipris et al. |
| 4,162,200 A | 7/1979 | Himmele et al. |
| 4,181,676 A | 1/1980 | Buysch et al. |
| 4,252,737 A | 2/1981 | Krimm et al. |
| 4,307,032 A | 12/1981 | Krimm et al. |
| 4,330,665 A | 5/1982 | Krimm et al. |
| 4,552,704 A | 11/1985 | Mark |
| 4,554,110 A | 11/1985 | Mark |
| 4,609,501 A | 9/1986 | Mark |
| 4,734,519 A | 3/1988 | Dunski et al. |
| 5,151,541 A | 9/1992 | Joerg et al. |
| 5,231,212 A | 7/1993 | Buysch et al. |
| 5,334,742 A | 8/1994 | Schon et al. |
| 5,344,954 A | 9/1994 | Schon et al. |
| 5,350,862 A | 9/1994 | Wagner et al. |
| 5,354,923 A | 10/1994 | Schon et al. |
| 5,359,118 A | 10/1994 | Wagner et al. |
| 5,360,923 A | 11/1994 | Nickel et al. |
| 5,508,442 A | 4/1996 | Wagner et al. |
| 6,387,222 B1 | 5/2002 | Tragut et al. |
| 6,930,195 B2 | 8/2005 | Buchanan et al. |
| 2006/0194978 A1 | 8/2006 | Murthy et al. |
| 2007/0219387 A1 | 9/2007 | Fukuoka et al. |
| 2007/0255069 A1 | 11/2007 | Fukuoka et al. |
| 2007/0265461 A1 | 11/2007 | Fukuoka et al. |

FOREIGN PATENT DOCUMENTS

| | | |
|---|---|---|
| DE | 22 22 488 A1 | 11/1972 |
| DE | 2 528 412 A1 | 1/1976 |
| DE | 33 02 525 A1 | 7/1984 |
| DE | 3 445 552 A1 | 7/1985 |
| DE | 3 445 553 A1 | 7/1985 |
| DE | 34 45 555 A1 | 7/1985 |
| DE | 40 36 594 A1 | 5/1992 |
| DE | 42 26 755 A1 | 2/1994 |
| DE | 42 26 756 A1 | 2/1994 |
| DE | 199 14 966 A1 | 10/2000 |
| EP | 0 000 879 | 3/1979 |
| EP | 0 000 880 | 3/1979 |
| EP | 1 082 A1 | 3/1979 |
| EP | 1 083 A1 | 3/1979 |
| EP | 39 452 A2 | 11/1981 |
| EP | 0180387 A2 | 5/1986 |
| EP | 0338760 A2 | 10/1989 |
| EP | 413 217 A2 | 2/1991 |
| EP | 0461274 A1 | 12/1991 |
| EP | 463 678 A2 | 1/1992 |
| EP | 530615 A2 | 3/1993 |
| EP | 546 428 A1 | 6/1993 |
| EP | 569 812 A1 | 11/1993 |
| EP | 581115 A2 | 2/1994 |
| EP | 592883 A1 | 4/1994 |
| EP | 628 553 A1 | 12/1994 |
| EP | 638 541 A1 | 2/1995 |
| EP | 767 518 A2 | 4/1997 |
| EP | 0781760 A1 | 7/1997 |

(Continued)

OTHER PUBLICATIONS

Fukuoka, S., et al., *A Novel Non-Phosgene Process for Polycarbonate Production from $CO_2$: Green and Sustainable Chemistry in Practice* (2010), Catal Surv Asia 14, pp. 146-163.

Tomishige, K., et al., *Novel route to propylene carbonate: selective synthesis from propylene glycol and carbon dioxide* (2004), Catalysis Letters, vol. 95, Nos. 1-2, pp. 45-49.

Gabriele, B., et al., A novel and efficient method for the catalytic direct oxidative carbonylation of 1,2- and 1,3-diols to 5-membered and 6-membered cyclic carbonates (2009), Tetrahedron Letters, 50, pp. 7330-7332.

(Continued)

*Primary Examiner* — Terressa Boykin

(74) *Attorney, Agent, or Firm* — Connolly Bove Lodge & Hutz LLP

(57) ABSTRACT

The present invention relates to a process for continuously preparing diaryl carbonates from dialkyl carbonates and at least one monohydroxyl compound in the presence of catalysts, and to the use thereof for preparation of polycarbonates. The alkylene glycol obtained in the preparation of the dialkyl carbonate used is recycled by oxidative carbonylation with carbon monoxide in the presence of a catalyst to give the cyclic alkylene carbonate which is in turn converted to the dialkyl carbonate. More particularly, the process utilizes the alkylene glycol obtained for the diphenyl carbonate preparation process (DPC process).

13 Claims, 4 Drawing Sheets

FOREIGN PATENT DOCUMENTS

| | | |
|---|---|---|
| EP | 889025 A1 | 1/1999 |
| EP | 1086940 A1 | 3/2001 |
| EP | 1174406 A1 | 1/2002 |
| EP | 1 237 842 A1 | 9/2002 |
| EP | 1 638 917 A2 | 3/2006 |
| EP | 1762559 A1 | 3/2007 |
| EP | 1762560 A1 | 3/2007 |
| EP | 1767516 A1 | 3/2007 |
| EP | 1767517 A1 | 3/2007 |
| EP | 1767518 A1 | 3/2007 |
| EP | 1775280 A1 | 4/2007 |
| GB | 1382313 A | 1/1975 |
| GB | 1499530 A | 2/1978 |
| JP | 54-063023 | 10/1977 |
| JP | 54/125617 A | 9/1979 |
| JP | 57/176 932 A | 10/1982 |
| JP | 61/1 72 852 A | 8/1986 |
| JP | 01-093580 A | 4/1989 |
| JP | 01093560 A | 4/1989 |
| JP | 2002-020351 A | 1/2002 |
| WO | WO-2004/016577 A1 | 2/2004 |
| WO | WO-2005/000776 A2 | 1/2005 |
| WO | WO-2006/033291 A1 | 3/2006 |
| WO | WO-2007/096343 A1 | 8/2007 |

OTHER PUBLICATIONS

Giannoccaro, P., et al., Interaction of $PdCl_2$-2-(β-diphenylphosphine)ethylpyridine Complex with Diols and CO: Synthesis of New Alkoxycarbonyl Complexes, Key Intermediates to Cyclic Carbonates (2006), Organometallics, 25, pp. 2872-2879.

Tam., W., Carbonylation of β-Aminoethanols, Diols, and Diol Amines (1986), J. Org. Chem. 51, pp. 2977-2981.

Ullmann's Encyclopädie der Technischen Chemie, 4th Ed., vol. 2, pp. 528-533.

Ullmann's Encyclopedia of Industrial Chemistry, 6th Ed., vol. 10, Chapters 6.4. and 6.5.

Chemie Ingenieur Technik (67) Nov. 1995.

Kister, H.Z., *Distillation—Design*, Chapter 6, pp. 259-268.

PROCESS FOR PREPARING DIARYL CARBONATES FROM DIALKYL CARBONATES

CROSS REFERENCE TO RELATED APPLICATIONS

Priority is claimed to German Patent Application No. 10 2010 042 937.6, which is incorporated herein by reference, in its entirety, for all useful purposes.

BACKGROUND

The field of the present invention relates to a process for continuously preparing diaryl carbonates from dialkyl carbonates and at least one monohydroxyl compound in the presence of catalysts, and to the use thereof for preparation of polycarbonates. The alkylene glycol obtained in the preparation of the dialkyl carbonate used is recycled by oxidative carbonylation with carbon monoxide in the presence of a catalyst to give the cyclic alkylene carbonate which is in turn converted to the dialkyl carbonate. More particularly, the process consists in the utilization of the alkylene glycol obtained for the diphenyl carbonate preparation process (DPC process).

It is known that diaryl carbonates, especially diphenyl carbonate, can be obtained by phase interface phosgenation (Schotten-Baumann reaction) of monophenols in an inert solvent in the presence of alkali and a catalyst. The use of solvents and sodium hydroxide solution is disadvantageous, since the aqueous alkali can cause partial hydrolysis of phosgene or chlorocarbonic esters, large amounts of sodium chloride are obtained as a by-product, and the solvent and catalyst have to be recovered.

The preparation of aromatic and aliphatic-aromatic carbonic esters (carbonates) by transesterification proceeding from aliphatic carbonic esters and monophenols is also known in principle. This is an equilibrium reaction wherein the equilibrium position is shifted almost entirely in the direction of the aliphatically substituted carbonates. It is therefore comparatively easy to prepare aliphatic carbonates from aromatic carbonates and alcohols. In order, however, to carry out the reaction in the reverse direction towards aromatic carbonates, it is necessary to shift the very unfavourable equilibrium effectively to the side of the aromatic carbonates, for which not only very active catalysts but also suitable process regimes have to be employed.

The processes known from the literature, for example EP-A 461 274, DE-A 42 26 755, DE-A 42 26 756, however, generally describe only those process steps in which the reaction to give the diaryl carbonate takes place by transesterification and/or disproportionation. WO-A 2006/033291, EP-A 1 775 280, EP-A 1 767 516, EP-A 1 767 517, EP-A 767 518, EP-A 1 762 559 and EP-A 1 762 560 additionally give hints with regard to the apparatus configurations of reaction columns for preparation of diaryl carbonates. For the economic viability of a process, however, not just the process sections in the region of the reaction but, in some cases to a much greater degree, the subsequent steps for workup are of relevance.

Since the preparation of diaryl carbonates by reaction of an aromatic hydroxyl compound with a dialkyl carbonate, as experience has shown, is energetically very demanding, measures for reducing the energy consumption likewise play an important role. In this regard, there are also some approaches in the literature to energetic and apparatus integration.

The preparation of dialkyl carbonates by transesterifying cyclic alkylene carbonate and alkyl alcohol is known and has been described many times. U.S. Pat. No. 6,930,195 B described this catalysed transesterification reaction as a two-stage equilibrium reaction. In the first reaction stage, the cyclic alkylene carbonate reacts with alkyl alcohol to give hydroxyalkyl alkyl carbonate as an intermediate. The intermediate is then converted in the second reaction stage with the aid of alkyl alcohol to give dialkyl carbonate and alkylene glycol.

For the industrial implementation of the dialkyl carbonate preparation process, the use of a reactive distillation column (also referred to hereinafter as transesterification column), which has already been described in documents including EP 530 615 A, EP 569 812 A and EP 1 086 940 A, has been found to be particularly favourable. In EP 569 812 A, the cyclic alkylene carbonate is introduced continuously into the upper part of the transesterification column, and the dialkyl carbonate-containing alkyl alcohol into the middle or lower part of the transesterification column. In addition, below the introduction of the dialkyl carbonate-containing alkyl alcohol, virtually pure alkyl alcohol is introduced. The high boiler mixture, which includes the alkylene glycol prepared as a by-product, is drawn off continuously at the bottom of the transesterification column. The low boiler mixture, which comprises the dialkyl carbonate prepared, is drawn off at the top of the transesterification column as dialkyl carbonate-alkyl alcohol mixture and subjected to a further purification step.

A disadvantage is the formation of the alkylene glycol as a coproduct, which can be used for the preparation of polyesters only with good optical properties (fibre quality). In order to achieve the good optical properties, it is therefore necessary to drive high expenditure for purification of the alkylene glycol, which adversely affects the economic viability of the process.

Therefore, the reaction of alkylene glycol with urea to give cyclic alkylene carbonate and ammonia has also already been described in EP 638 541 B1. A disadvantage here is that ammonia does not find use for polycarbonate preparation and the conversion of ammonia and carbon dioxide to urea is barely economically viable, if at all.

It is known that the oxidative carbonylation of monoalcohols with carbon monoxide and oxygen in the presence of Co catalysts and Cu catalysts such as CuCl leads to dialkyl carbonate, as described in EP 463 678 A2 or EP 413 217 A2. A disadvantage is the corrosive properties of the catalyst system.

U.S. Pat. No. 4,131,521 describes the electrochemical oxidation of dialcohols such as ethylene glycol to give ethylene carbonate. A disadvantage is the formation of hydrogen as a by-product, which does not find use in polycarbonate preparation.

Tetrahedron Letters 50, 7330 (2009) describes the reaction of alkylene glycols with carbon monoxide and oxygen with $PdI_2/KI$ as a catalyst system. Disadvantages are the low turnover number (TON) and the low selectivity of 84%.

EP 781 760 A1 describes a continuous process for preparing aromatic carbonates by reacting a dialkyl carbonate with an aromatic hydroxyl compound in the presence of a catalyst and continuously removing the aromatic carbonate formed in the reaction, the alcoholic by-products, the dialkyl carbonate and the aromatic hydroxyl compound, the dialkyl carbonate and the aromatic hydroxyl compound being recycled into the reaction.

EP 1 638 917 A1 describes a process for recovering a product from a waste stream by contacting with an alkyl alcohol, the product recovered comprising diaryl carbonate, aromatic alcohol, alkyl salicylate and alkyl alcohol. One disadvantage of the process described is that the reaction is effected in three stages, which makes it very complicated. Another is that high-boiling waste streams are obtained at two points. Removal of the catalyst before the isolation of the diaryl carbonate gives rise to the first waste stream, and the subsequent workup consisting of two distillation columns to the second waste stream. The workup for isolation of the diaryl carbonate is thus very demanding both in apparatus and energetic terms. In addition, the quality of the diaryl carbonate thus prepared at 99.5% by weight is very poor and it is unsuitable for the preparation of polycarbonate. The separation of the mixture of alcohol of reaction and dialkyl carbonate obtained in the reaction is not described either.

WO-A 2005/000776 describes a process for preparing an alkyl aryl ether which is formed in the reaction of a dialkyl carbonate with an aromatic hydroxyl compound. In this process, diaryl carbonate is additionally also obtained. The process structure comprises three reaction columns and two further distillation columns for the purpose of isolating the alkyl aryl ether. The fact that a controlled purification of the alkyl aryl ether is an aim in the process described here leads to the conclusion that the amount formed in the reaction is high. In the preparation of diaryl carbonates, however, the recovery of a high-purity alkyl aryl ether is not first priority, and the aim is instead minimum formation of this by-product obtained in the transesterification. Moreover, the reaction regime comprising three reaction stages is very complicated, and no information is given with regard to the workup of the diaryl carbonate and the separation of the mixture which is obtained in the reaction and comprises dialkyl carbonate and alcohol of reaction. EP-A 1 237 842 A1 also describes a comparable process, and therefore the disadvantages already mentioned likewise apply to this.

WO-A 2004/016577 describes a process for preparing aromatic carbonates from dialkyl carbonate and an aromatic hydroxyl compound in the presence of a catalyst in a plurality of separate and series-connected reaction zones of a reactor arrangement, wherein the heat of condensation obtained in the condensation of the vapour stream of the last reaction zone is used to heat the liquid stream introduced into the first reaction zone. However, a disadvantage of this process is the complicated reactor arrangement. In addition, the energetic integration of this process is in need of improvement and is limited only to the process section of reaction. Subsequent steps for the workup are not described.

JP-A 2002-020351 describes a batchwise process for preparing diaryl carbonate, from which heat can be utilized for steam raising. However, disadvantages of this process are the batchwise performance and the reactor arrangement used for the reaction, which has an attached distillation column. Subsequent steps for the workup are not described.

The chemical oxidation of alcohols with carbon monoxide and oxygen to give alkyl carbonates is known in principle.

For instance, EP 463 678 A2 describes the oxidative carbonylation of alcohols with carbon monoxide and oxygen in the presence of Co catalysts and Cu catalysts such as CuCl to give dialkyl carbonate.

The oxidative carbonylation of dialcohols with carbon monoxide and oxygen to give alkylene carbonate is also known.

U.S. Pat. No. 4,131,521 describes the formation of ethylene carbonate in 5 to 10% yield by electrochemical oxidation of ethylene glycol in the presence of $NH_4Br$. Disadvantages are the low economic viability of an electrochemical oxidation and the formation of hydrogen as a by-product.

DE A 22 22 488 describes a process for preparing cyclic glycol carbonates from glycols with $CO/O_2$ in the presence of copper ions. Disadvantages are the short service life of the catalyst with a TON below 93 and the low activity of the catalyst with a turnover frequency below 30 $mol_{glycol} \cdot mol_{Cu}^{-1} \cdot h^{-1}$.

Organometallics, 25, 2872 (2006) describes the preparation of ethylene carbonate from ethylene glycol. A disadvantage is that the expensive Pd catalyst is required in stoichiometric amounts.

Tetrahedron Lett. 50, 7330 (2009) describes the oxidative carbonylation of dialcohols such as ethylene glycol to give ethylene carbonate with $PdI_2/KI$ as a catalyst formulation. In spite of a great CO excess, only a moderate TON is mentioned.

J. Org. Chem. 51. 2977 (1986) describes the conversion of ethylene glycol and 1-phenylethanediol to the corresponding cyclic carbonates. A disadvantage is the use of metal salts as an oxidant in stoichiometric amounts.

There was accordingly still a need to provide a process for preparing aromatic carbonates, preferably diaryl carbonates, which includes recycling of the alkylene glycol by-product formed, which does not have the disadvantages specified above and in which, compared to the known processes specified above, avoidance of the coproduct is possible or can be achieved in an efficient manner.

The problem underlying the invention was accordingly to provide a process for preparing aromatic carbonates, preferably diaryl carbonates, which comprises preparation of the dialkyl carbonate used with recycling of the alkylene glycol obtained as a coproduct.

BRIEF DESCRIPTION OF PREFERRED EMBODIMENTS

An embodiment therefore provides a process for preparing diaryl carbonates and polycarbonates proceeding from dialkyl carbonates and monophenols, which is characterized in that the alkylene glycol which forms in the preparation of the dialkyl carbonate used from cyclic alkylene carbonate and alkyl alcohol is recycled by reaction with carbon monoxide to give the alkylene carbonate, which is subsequently used again with the alkyl alcohol to prepare the dialkyl carbonate. The monophenol which is released in the preparation of solvent-free polycarbonate by transesterification of diaryl carbonates and bisphenols can in turn be used to prepare the diaryl carbonate.

The overall process according to an embodiment of the invention is flexible, simple to perform and gives products in high purity, which are extremely important for the overall process with simultaneous reduction of the environmental pollution by reuse, comprising the following process steps (cf. FIG. 1):

(a) preparing alkylene carbonate by reaction of alkylene oxide with carbon dioxide, (b) reacting the alkylene carbonate formed in step (a) with at least one alkyl alcohol in the presence of a catalyst, and optionally organic solvent, to form at least one dialkyl carbonate and alkylene glycol, (c) removing and working up at least a portion of the at least one dialkyl carbonate formed in step (b), (d) removing and optionally purifying at least a portion of the alkylene glycol formed in step (b), (e) oxidatively carbonylating at least a portion of the alkylene glycol removed in step (d) with carbon monoxide to give the alkylene carbonate with formation of water, (f) removing and optionally purifying at least a portion of the alkylene carbonate formed in step (e), (g) recycling at least a portion of the alkylene carbonate prepared in step (f) into the preparation of dialkyl carbonate in step (b), (h) reacting at least a portion of the dialkyl carbonate prepared in step (c) with a monophenol to give the alkyl aryl carbonate and/or diaryl carbonate and alkyl alcohol; optionally recycling at least a portion of the alkyl alcohol formed in step (h) into step (b), (i) disproportionating at least a portion of the alkyl aryl carbonate prepared in step (h) to give the diaryl carbonate and dialkyl carbonate and optionally recycling at least a portion of the diaryl carbonate and/or dialkyl carbonate prepared in step (i) into step (b), (j) transesterifying at least a portion of the diaryl carbonate prepared in step (i) with a bisphenol to give a oligo-/polycarbonate and a monophenol; optionally recycling at least a portion of the monophenol formed in step (j) into step (h).

BRIEF DESCRIPTION OF THE DRAWINGS

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF PREFERRED EMBODIMENTS

Figure 1:
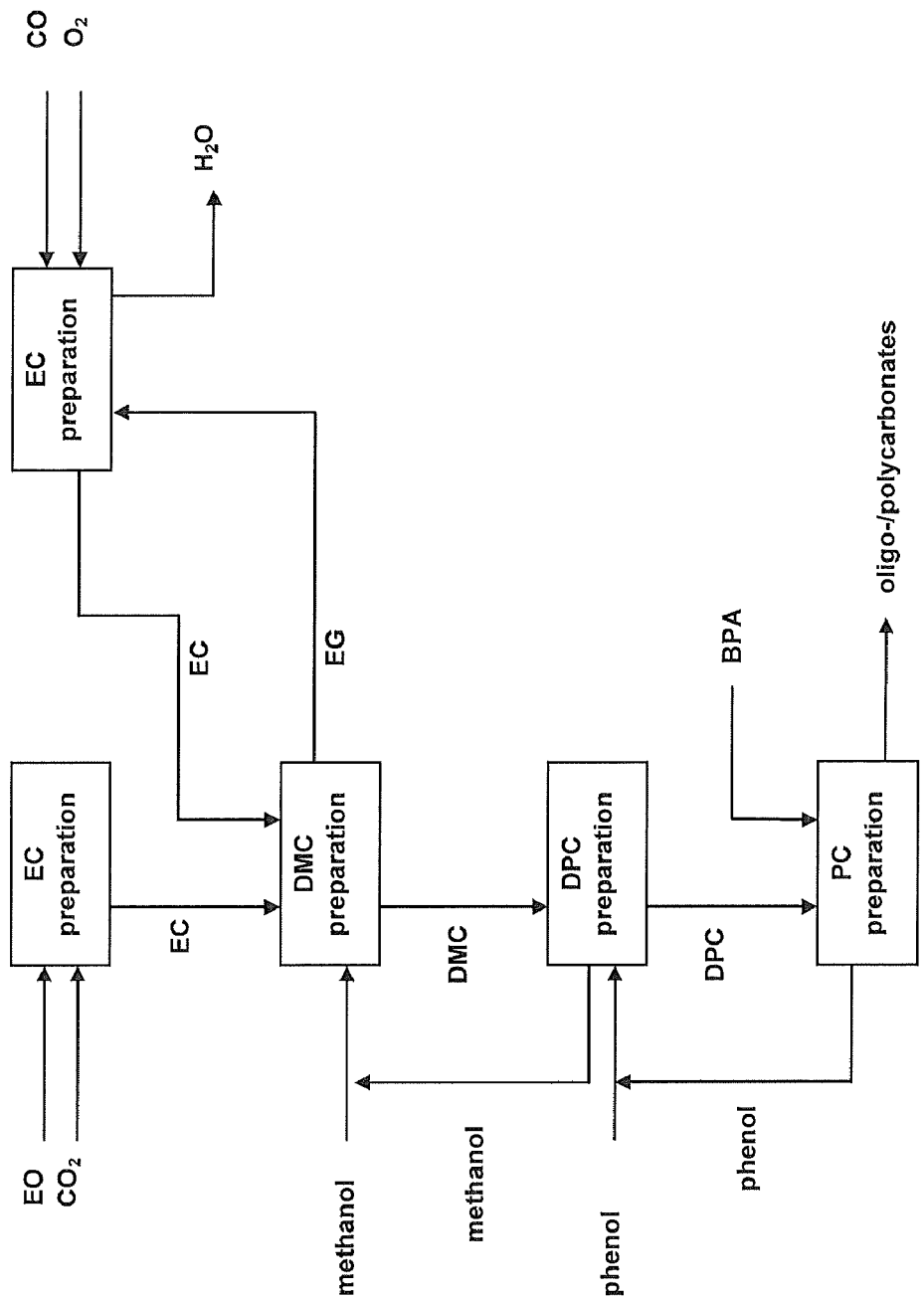
FIG. 1 shows an integrated process for preparing polycarbonate and recycling of the ethylene glycol obtained and of the phenol.

As used herein, the singular terms "a" and "the" are synonymous and used interchangeably with "one or more" and "at least one," unless the language and/or context cleary indicates otherwise. Accordingly, for example, reference to "a catalyst" herein or in the appended claims can refer to a single catalyst or more than one catalyst. Additionally, all numerical values, unless otherwise specifically noted, are understood to be modified by the word "about."

Cyclic alkylene carbonates used in the context of the invention, as prepared in step (a) and used in step (b), are preferably those with the formula (I):

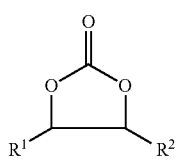

(I)

where, in the formula (I), $R^1$ and $R^2$ may each independently be hydrogen, substituted or unsubstituted $C_1$-$C_4$-alkyl, substituted or unsubstituted $C_2$-$C_4$-alkenyl or substituted or unsubstituted $C_6$-$C_{12}$-aryl and $R^1$ and $R^2$ together with the two five-membered ring carbon atoms may be a saturated carbocyclic ring having 5-8 ring members. Preference is given to ethylene carbonate, propylene carbonate and butylene carbonate, particular preference to ethylene carbonate and propylene carbonate, very particular preference to ethylene carbonate.

The cyclic alkylene carbonates are reacted with alcohols of the form $$R^3\text{—OH}$$

to give dialkyl carbonates, where $R^3$ is a straight-chain or branched $C_1$-$C_4$-alkyl.

This reaction forms an alkylene glycol of the formula $R^2(OH)_2$ as a by-product, which is removed in step (d) from the dialkyl carbonate main product and optionally purified.

Dialkyl carbonates used with preference in the context of the invention are those of the formula (II)

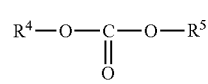

(II)

where $R^4$ and $R^5$ are each independently linear or branched, optionally substituted $C_1$-$C_{34}$-alkyl, preferably $C_1$-$C_6$-alkyl, more preferably $C_1$-$C_4$-alkyl. $R^4$ and $R^5$ may be the same or different. $R^4$ and $R^5$ are preferably the same.

$C_1$-$C_4$-Alkyl in the formula (II) is, for example, methyl, ethyl, n-propyl, isopropyl, n-butyl, sec-butyl, tert-butyl; $C_1$-$C_6$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl; $C_1$-$C_{34}$-alkyl is additionally, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies to the corresponding alkyl radical, for example in aralkyl or alkylaryl radicals. Alkylene radicals in the corresponding hydroxyalkyl or aralkyl or alkylaryl radicals are, for example, the alkylene radicals corresponding to the above alkyl radicals.

Aryl is a carbocyclic aromatic radical having 6 to 34 skeleton carbon atoms. The same applies to the aromatic moiety of an arylalkyl radical, also known as an aralkyl radical, and also to aryl constituents of more complex groups, for example arylcarbonyl radicals.

Arylalkyl or aralkyl is in each case independently a straight-chain, cyclic, branched or unbranched alkyl radical as defined above, which may be mono-, poly- or persubstituted by aryl radicals as defined above.

The above lists are illustrative and should not be understood as a limitation.

Preferred dialkyl carbonates are dimethyl carbonate, diethyl carbonate, di(n-propyl)carbonate, di(isopropyl)carbonate, di(n-butyl)carbonate, di(sec-butyl)carbonate, di(tert-butyl)carbonate or dihexyl carbonate. Particular preference is given to dimethyl carbonate or diethyl carbonate. Very particular preference is given to dimethyl carbonate.

The usable transesterification catalysts for the preparation of dialkyl carbonates in step (b) from the cyclic alkylene carbonate from step (a) and the alcohol are those known to the person skilled in the art, for example hydrides, oxides, hydroxides, alkoxides, amides or salts of alkali metals, such as lithium, sodium, potassium, rubidium and caesium, preferably of lithium, sodium and potassium, more preferably of sodium and potassium (U.S. Pat. No. 3,642,858 A, U.S. Pat. No. 3,803,201 A, EP 1 082 A). In the case of use of the alkoxides, they can also be formed in situ in accordance with the invention, by using the elemental alkali metals and the alcohol to be converted in accordance with the invention. Salts of the alkali metals may be those of organic or inorganic acids, such as those of acetic acid, propionic acid, butyric acid, benzoic acid, stearic acid, carbonic acid (carbonates or hydrogencarbonates), of hydrochloric acid, hydrobromic acid or hydriodic acid, nitric acid, sulphuric acid, hydrofluoric acid, phosphoric acid, hydrogen cyanide, hydrogen thiocyanate, boric acid, stannic acid, $C_1$-$C_4$-stannoic acids or antimony acids. Preferred compounds of the alkali metals are the oxides, hydroxides, alkoxides, acetates, propionates, benzoates, carbonates and hydrogencarbonates; particular preference is given to using hydroxides, alkoxides, acetates, benzoates or carbonates. Such alkali metal compounds (optionally formed in situ from the free alkali metals) are used in amounts of 0.001 to 2% by weight, preferably 0.003 to 1.0% by weight, more preferably 0.005 to 1.0% by weight, based on the reaction mixture to be converted.

Suitable catalysts for the process in step (b) are also thallium(I) and thallium(III) compounds, such as the oxides, hydroxides, carbonates, acetates, bromides, chlorides, fluorides, formates, nitrates, cyanates, stearates, naphthenates, benzoates, cyclohexylphosphonates, hexahydrobenzoates, cyclopentadienylthallium, thallium methoxide, thallium ethoxide, preferably Tl(I) oxide, Tl(I) hydroxide, Tl(I) carbonate, Tl(I) acetate, Tl(III) acetate, Tl(I) fluoride, Tl(I) formate, Tl(I) nitrate, Tl(I) naphthenate and Tl(I) methoxide (EP 1 083). The amounts of thallium catalyst are not particularly critical. They are generally 0.0001-10% by weight, preferably 0.001-1% by weight, based on the overall reaction mixture. In the process according to the invention, it is also possible to use nitrogen bases as catalysts (U.S. Pat. No. 4,062,884). Examples include sec- or tert-amines such as triethylamine, tributylamine, methyldibenzylamine, dimethylcyclohexylamine among others.

The amounts of the nitrogen bases used in step (b) are from 0.01 to 10% by weight, preferably from 0.1 to 5% by weight, more preferably from 0.1 to 1% by weight, based on the overall reaction mixture. Usable catalysts in accordance with the invention are also compounds from the group of the phosphines, stibines, arsines or the divalent sulphur and selenium compounds, and the onium salts thereof (EP 180 387, U.S. Pat. No. 4,734,519).

Examples include the following: tributylphosphine, triphenylphosphine, diphenylphosphine, 1,3-bis(diphenylphosphino)propane, triphenylarsine, trimethylarsine, tributylarsine, 1,2-bis(diphenylarsino)ethane, triphenylantimony, diphenyl sulphide, diphenyl disulphide, diphenyl selenide, tetraphenylphosphonium halide (Cl, Br, I), tetraphenylarsonium halide (Cl, Br, I), triphenylsulphonium halide (Cl, Br) etc.

The amounts used of this catalyst group are in the range from 0.1 to 10% by weight, preferably from 0.1 to 5% by weight, more preferably in the range from 0.1 to 2% by weight, based on the overall reaction mixture.

Additionally usable are complexes or salts of tin, of titanium or of zirconium. Examples of such systems are butylstannoic acid, tin methoxide, dimethyltin, dibutyltin oxide, dibutyltin dilaurate, tributyltin hydride, tributyltin chloride, tin(II) ethylhexanoate, zirconium alkoxides (methyl, ethyl, butyl), zirconium(IV) halides (F, Cl, Br, I), zirconium nitrate, zirconium acetylacetonate, titanium alkoxides (methyl, ethyl, isopropyl), titanium acetate, titanium acetylacetonate etc.

The amounts usable in accordance with the invention are 0.1 to 10% by weight, preferably 0.1 to 5% by weight, based on the overall mixture.

In the present process, it is additionally possible to use, in step (b), bifunctional catalysts of the formula (III)

$$[A_aX_b]_m \cdot [B_cY_d]_n \qquad \text{(III)}.$$

In these bifunctional catalysts, the molar ratio of the two components in square brackets is expressed by the indices in and n. These indices may each independently assume values of 0.001-1, preferably 0.01-1, more preferably 0.05-1 and most preferably 0.1-1. Between the square brackets are neutral salts each composed of a cation and an anion. The indices a and b are each independently integers of 1-5; the indices c and d are each independently integers of 1-3, and the valence requirements of the cations and anions for formation of such neutral salts should be met. In addition, in (VI), A is the cation of a metal which belongs to the third period and group IIa, the fourth period and group IIa, IVa-VIIIa, Ib or IIb, the fifth period and group IIa, IVa-VIIa or IVb, or the sixth period and group IIa-VIa of the Periodic Table of the Elements in the short period form.

The possible metals for the cation A are inferred by the person skilled in the art from the customary representations of the Periodic Table of the Elements (Mendeleev) in the short period form. A is preferably the cation of one of the metals Mg, Ca, Sr, Ba, Zn, Cu, Mn, Co, Ni, Fe, Cr, Mo, W, Ti, Zr, Sn, Hf, V and Ta, preferably the cation of one of the metals Mg, Ca, Zn, Co, Ni, Mn, Cu and Sn. Apart from the non-complexed cations of the metals mentioned, cationic oxo complexes of the metals mentioned are also an option, for example titanyl $TiO^{++}$ and chromyl $CrO_2^{++}$.

The anion X belonging to the cation A is that of an inorganic or organic acid. Such an inorganic or organic acid may be monobasic or dibasic or tribasic. Such acids and their anions are known to those skilled in the art. Examples of anions of monobasic inorganic or organic acids are: fluoride, bromide, chloride, iodide, nitrate, the anion of an alkanecarboxylic acid having 1-18 carbon atoms and benzoate; examples of anions of dibasic inorganic or organic acids are: sulphate, oxalate, succinate, fumarate, maleate, phthalate and so forth; examples of tribasic inorganic or organic anions are: phosphate or citrate. Preferred anions X in the catalyst of the formula (III) are: fluoride, chloride, bromide, iodide, sulphate, nitrate, phosphate, formate, acetate, propionate, oxalate, butyrate, citrate, succinate, fumarate, maleate, benzoate, phthalate, decanoate, stearate, palmitate, and laurate. Particularly preferred anions X are: chloride, bromide, iodide, acetate, laurate, stearate, palmitate, decanoate, nitrate and sulphate.

A useful cation B in the catalysts of the formula (III) is one from the group of the alkali metal or alkaline earth metal cations, the quaternary ammonium, phosphonium, arsonium or stibonium cations and the ternary sulphonium cations.

Alkali metal/alkaline earth metal cations in this context include: the lithium, sodium, potassium, rubidium, caesium, magnesium, calcium, strontium and barium cation, preferably the alkali metal cations mentioned, more preferably the sodium and the potassium cation.

Preferred cations B are those of the formula (IV)

in which
Q$^1$ is N, P, As or Sb and
R$^6$, R$^7$, R$^8$ and R$^9$ are each independently straight-chain or branched C$_1$-C$_{18}$ or C$_7$-C$_{12}$-aralkyl and one of the R$^6$-R$^9$ radicals may also be. B is more preferably a cation of the formula (V)

in which
Q$^2$ is N or P, preferably N.

Most preferably, in the context of the formulae (IV) and (V), the R$^6$, R$^7$, R$^8$ and R$^9$ radicals are replaced by the R$^{16}$, R$^{17}$, R$^{18}$ and R$^{19}$ radicals, which are each independently straight-chain or branched C$_1$-C$_{18}$-alkyl or C$_7$-C$_8$-aralkyl, and one of the R$^{16}$ to R$^{19}$ radicals may also be phenyl. Most preferably, in addition, the R$^{16}$, R$^{17}$, R$^{18}$ and R$^{19}$ radicals are replaced by the R$^{26}$, R$^{27}$, R$^{28}$ and R$^{29}$ radicals, which are each independently C$_1$-C$_8$-alkyl or benzyl, and one of the R$^{26}$ to R$^{29}$ radicals may also be phenyl.

Straight-chain or branched C$_1$-C$_{18}$-alkyl is, for example, methyl, ethyl, propyl, isopropyl, butyl, isobutyl, hexyl, octyl, dodecyl, hexadecyl or octadecyl. Preferred alkyl has 1-12 carbon atoms; especially preferred alkyl has 1-8 carbon atoms.

C$_7$-C$_{12}$-Aralkyl is, for example, benzyl, phenylethyl, phenylpropyl, naphthylmethyl or naphthylethyl; preferred aralkyl is benzyl or phenylethyl; most preferred aralkyl is benzyl.

C$_6$-C$_{12}$-Aryl is, for example, phenyl, naphthyl or biphenylyl, preferably phenyl.

The anion Y in the catalyst of the formula (IV) is a halide ion, such as fluoride, chloride, bromide or iodide, preferably bromide or iodide, more preferably iodide. However, it can also be defined as other anions mentioned under X if the anion X in the specific case is bromide or iodide.

The bifunctional catalyst of the formula (IV) is used in an amount of 0.005-5% by weight, preferably 0.01-3% by weight, more preferably 0.01-1% by weight, based on the overall transesterification mixture.

The process for preparing dialkyl carbonate from alkylene carbonate and alkyl alcohol can be performed continuously or batchwise. Preference is given to a continuous mode of operation.

The reaction of alkyl alcohol and alkylene carbonate to give dialkyl carbonate and alkylene glycol can be performed in different kinds of apparatus: columns, tubular reactors, reactors with attached columns etc., in cocurrent or countercurrent. Preference is given to performing the reaction in one or more columns in countercurrent, referred to hereinafter as transesterification column.

In the process, the cyclic alkylene carbonate compound(s) and the alkyl alcohol(s) are used preferably in a molar ratio of 1:0.1 to 1:40, more preferably of 1:1.0 to 1:30, most preferably of 1:2.0 to 1:20. The molar ratio specified does not take account of the recycling of cyclic alkylene carbonate compound or alcohol into the transesterification column via one or more top condenser(s) or one or more of any reboiler(s) present.

The catalyst is preferably introduced into the column via an introduction site arranged above the introduction sites of the alkyl alcohol, together with the stream comprising the cyclic alkylene carbonate in dissolved or suspended form into the transesterification column. Alternatively, the catalyst can also be metered in separately, for example dissolved in the alkyl alcohol, in the alkylene glycol or in a suitable inert solvent. In the case of use of heterogeneous catalysts, they can be used in a mixture with random packings, in a suitable shape instead of random packings or as a bed on any column trays installed.

The conversion of alkylene carbonate and alkyl alcohol to dialkyl carbonate and alkylene glycol takes place almost completely in the transesterification column. In preferred embodiments of the process for preparing dialkyl carbonate, the liquid stream withdrawn at the bottom of this transesterification column—optionally after concentration—can be subjected to a further reaction and/or purification in one or more further steps. Preferably, individual steps, or all such further steps, can be effected in one or more further columns or in other apparatus suitable for purification, such as falling-film evaporators or thin-film evaporators.

Useful transesterification columns or any second or further column(s) include columns known to those skilled in the art. These are, for example, distillation and rectification columns, preferably reactive distillation and reactive rectification columns.

The transesterification column preferably comprises at least one rectifying section in the upper part of the column and at least one reaction zone below the rectifying section. Each of the two sectors independently has preferably 0 to 30, preferably 0.1 to 30, theoretical plates each.

In preferred embodiments, the transesterification column has at least one stripping section below a reaction zone.

The transesterification column may further preferably be equipped with one or more reboiler(s). When the transesterification column is designed with a stripping section, preference is given to additionally using a reboiler which fully or partly evaporates the liquid effluxing from the stripping section. This fully or partially evaporated liquid stream is recycled fully or partly back into the transesterification column. In the case of an embodiment without a stripping section, in any reboiler used, the liquid effluxing from the reaction zone is evaporated fully or partly and recycled fully or partly back into the transesterification column.

The rectifying section(s) may, in preferred embodiments, be accommodated in the transesterification column together with the reaction section(s) and optionally at least one stripping section. In this case, the vaporous mixture coming from the reaction zone(s) is passed from below into a lower sector of the rectifying section and/or if appropriate into the lower rectifying section, which depletes the alkylene carbonate or alkylene glycol.

Below the reaction zone and any stripping section present, a mixture comprising alkylene glycol, excess or unconverted alkylene carbonate, alkyl alcohol, dialkyl carbonate, transesterification catalysts and high-boiling compounds which form in the reaction or are already present in the reactants is obtained. When a stripping section is used, the content of low-boiling compounds, for example dialkyl carbonate and alcohol, is reduced, forming further dialkyl carbonate and alkylene glycol, but also dialkylene glycol and further high-boiling compounds, under some circumstances in the presence of the transesterification catalyst. The energy required for this purpose is preferably supplied by one or more vaporizers.

In all sections of the transesterification column, i.e. both in the rectifying section and any stripping section, and in the reaction zone, random packings or structured packings can be used. The random packings or structured packings for use are those customary for distillations, as described, for example, in Ullmann's Encyclopädie der Technischen Chemie, 4th ed., vol. 2, p. 528 ff. Examples of random packings include Raschig or Pall and Novalox rings, Berl, Intalex or Torus saddles, Interpack bodies, and examples of structured packings include sheet metal and fabric packings (for example BX packings, Montz Pak, Mellapak, Melladur, Kerapak and CY packing) made of various materials, such as glass, stoneware, porcelain, stainless steel, plastic. Preference is given to random packings and structured packings which have a large surface area, good wetting and sufficient residence time of the liquid phase. These are, for example, Pall and Novalox rings, Berl saddles, BX packings, Montz Pak, Mellapak, Melladur, Kerapak and CY packings.

Alternatively suitable are also column trays, for example sieve trays, bubble-cap trays, valve trays, tunnel-cap trays. In the reaction zone(s) of the transesterification column, particular preference is given to column trays with high residence times coupled with good mass transfer, for example bubble-cap trays, valve trays or tunnel-cap trays with high overflow weirs. The number of theoretical plates of the reaction zone is preferably 3 to 50, more preferably 10 to 50 and most preferably 10 to 40. The liquid holdup is preferably 1 to 80%, more preferably 5 to 70% and most preferably 7 to 60% of the internal column volume of the reaction zone. The more exact design of the reaction zone(s), of any stripping section to be used and of the rectifying section(s) can be undertaken by the person skilled in the art.

The temperature of the reaction zone(s) is preferably in the range from 20 to 200° C., more preferably from 40 to 180° C., most preferably from 50 to 160° C. It is advantageous to perform the inventive transesterification not only at standard pressure, but also at elevated or reduced pressure. The pressure in the reaction zone is therefore preferably in the range of 0.2 to 20 bar, more preferably 0.3 to 10 bar, most preferably 0.4 to 5 bar. The pressure figures given above and below—unless explicitly stated otherwise—are absolute pressure figures.

Preferably, the vapor mixture which comprises dialkyl carbonate and alkyl alcohol and is withdrawn at the top of the transesterification column in the process for preparing the dialkyl carbonate, after condensation at the top of the transesterification column, is supplied fully or partly to at least one further process step comprising at least one distillation column for separation of dialkyl carbonate and alkyl alcohol.

The dialkyl carbonate and the alkyl alcohol are preferably separated by distillation in one or more distillation columns or in a combination of distillation and membrane separation—referred to hereinafter as hybrid process (see, for example, U.S. Pat. No. 4,162,200 A, EP 581 115 B1, EP 592 883 B1 and WO 2007/096343A1).

When alkyl alcohol and dialkyl carbonate form an azeotrope (e.g. methanol and dimethyl carbonate), it is also possible to use a two-stage process, for example a two-pressure process, an extractive distillation, a heteroazeotrope distillation with a low-boiling azeotroping agent, or a hybrid process. Particular preference is given to employing the two-pressure process or a hybrid process.

Very particular preference is given to performing the separation of the dialkyl carbonate and the alkyl alcohol—even in the case that the dialkyl carbonate and the alkyl alcohol form an azeotrope—in a single distillation column. This distillation column is operated at a pressure higher than the pressure of the transesterification column(s). The operating pressure of the distillation column is in the range from 1 to 50 bar, preferably between 2 and 20 bar. At the bottom of the distillation column the virtually pure dialkyl carbonate is withdrawn, and at the top a mixture of dialkyl carbonate and alkyl alcohol. This mixture is supplied fully or partly to the transesterification column(s). When the process for preparing dialkyl carbonate is coupled with a process for preparing diaryl carbonate which is formed by transesterification of this dialkyl carbonate with an aromatic hydroxyl compound, a portion of the mixture of dialkyl carbonate and alkyl alcohol which is withdrawn at the top of the distillation column can be sent to an appropriate workup step for alkyl alcohol and dialkyl carbonate in the process stage for preparation of dialyl carbonate.

In a particularly preferred version, when the dialkyl carbonate and the alkyl alcohol form an azeotrope, this workup step is a two-pressure process. Such processes are known in principle to those skilled in the art (cf., for example, Ullmann's Encyclopedia of Industrial Chemistry, $6^{th}$ edition, Vol. 10, Chap. 6.4. and 6.5; Chemie Ingenieur Technik (67) 11/95).

When alkyl alcohol and dialkyl carbonate form an azeotrope, the distillate of a first distillation column of the process step for separating dialkyl carbonate and alkyl alcohol preferably has virtually azeotropic composition. In this case, it is preferably fed, in a two-pressure process, to at least one further distillation column which operates at an operating pressure below that of the first distillation column. As a result of the different operating pressure, the position of the azeotrope shifts toward lower proportions of alkyl alcohol. The bottom product obtained from this second distillation column or these further distillation column(s) is alkyl alcohol in a purity of 90 to 100% by weight, based on the total weight of the isolated bottom product, and the distillate obtained is a virtually azeotropic mixture. The second distillation column or further distillation column(s) which work at lower operating pressure is/are, in very particularly preferred embodiments, preferably operated with the heat of condensation of the top condenser(s) of the first distillation column.

The operating pressure of the second distillation column, known as alkyl alcohol column, is preferably selected such that it can be operated with the waste heat of the dialkyl carbonate column. The operating pressure is between 0.1 and 1 bar, preferably between 0.3 and 1 bar. The operating pressure of the dialkyl carbonate column is in the range of 1 to 50 bar, preferably between 2 and 20 bar.

At the bottom of the transesterification column, a mixture comprising essentially alkylene glycol and small amounts of alkyl alcohol, dialkyl carbonate, alkylene carbonate and high boilers (for example dialkylene glycol) is withdrawn. If a homogeneous catalyst is used, it is likewise present in this mixture. This mixture is sent to a further workup in order to purify alkylene glycol, to substantially discharge unwanted components from the process, and to fully or partly recycle any homogeneous catalyst used or to discharge it completely from the process.

Any alkylene carbonate still present in the mixture can be reacted with water in the presence of any homogeneous catalyst still present or in the presence of a heterogeneous catalyst to give alkylene glycol (e.g. EP 889025). In addition, it is also possible to react alkylene carbonate with alkylene glycol to give dialkylene glycol and carbon dioxide (e.g. EP 1174406). These reactions are preferably performed in columns. The reaction to give dialkylene glycol takes place to a minor extent even at the moderate temperatures at which the transesterification takes place in the transesterification column, and can be enhanced by suitable selection of (increase in) the temperature and residence time in the apparatuses to which the bottoms of the transesterification column are supplied.

Preferably, the further reaction of the alkylene carbonate is not forced. After preferably distillative removal of the low-boiling components, a mixture essentially consisting of alkylene glycol and alkylene carbonate is removed from the remaining product stream, and supplied to the step of oxidative carbonylation (step e)).

The preparation of cyclic alkylene carbonate from alkylene oxide and carbon dioxide in step (a) is also known and has been described many times.

Alkylene oxides used in the context of the invention are ethylene oxide, propylene oxide and butylene oxide, preferably ethylene oxide and propylene oxide, more preferably ethylene oxide.

The catalysts used for the transesterification of alkylene oxides with carbon dioxide may be virtually all of those proposed to date, such as alkali metal and alkaline earth metal bromides and iodides, guanidines and the hydrobromides or hydroiodides thereof, tetraalkylammonium bromides and iodides, phosphonium bromides and iodides, pyridinium halides, sulphonium, stibonium and arsonium halides, zinc and lead halides, alkyltin compounds or mixtures of alkali metal halides with halides of divalent metal ions. Preferably, the catalysts used are: alkali metal bromides and iodides, tetraalkylammonium bromides and iodides, phosphonium halides, guanidinium halides and mixtures of alkali metal halides with halides of divalent metals, for example zinc halides.

Preference is given to performance in an adiabatic procedure, as described, for example, in EP 546 428 A1 in a bubble column reactor EP 628 553 A1.

The process is performed within the temperature range from 110 to 200° C., preferably 110 to 190° C., more preferably 110 to 180° C. The pressure for the process according to the invention is 2 to 200 bar, preferably 5 to 80 bar, more preferably 8 to 60 bar.

The alkylene glycol removed and optionally purified in step d) is subjected to an oxidative carbonylation in the presence of carbon monoxide (step (e)) and converted to alkylene carbonate.

The process according to the invention is preferably performed as follows: the reaction mixture is heated to the desired reaction temperature and the reaction is started by introducing a carbon monoxide/oxygen gas mixture into the reaction solution. The steps can also be performed in reverse sequence.

The composition of the gas mixture can be selected arbitrarily within wide limits. Instead of oxygen it is also possible to use an oxygen-containing gas mixture, for example including air, or the gas mixture can optionally be diluted with an inert gas such as nitrogen, argon or carbon dioxide. The ratio of carbon monoxide, oxygen and inert gas is preferably outside the explosive range. In general, a molar $CO/O_2$ ratio of 100:1 to 0.01:1, preferably 50:1 to 0.1:1, more preferably 8:1 to 1:1 is used. In the case of inert gases, the partial pressure ratio of the active gases to inert gas is 98:2 to 2:98, preferably 95:5 to 20:80, more preferably 95:5 to 50:50.

The reaction gases are introduced into the liquid present in the reactor. For better mixing and dispersion of the reaction gases in the reactor, in a preferred embodiment, it is possible to stir mechanically. Suitable reactor types are stirred tanks, stirred autoclaves or bubble reactors or bubble columns, which can appropriately be heated and if desired additionally provided with a stirrer apparatus.

The process according to the invention can be performed within a wide pressure and temperature range. In general, the temperature may be in the range from 0 to 200° C., preferably from 60 to 150° C., more preferably from 80 to 120° C. The reaction is appropriately performed under elevated pressure, generally at a pressure of 1 to 200 bar, preferably 5 to 100 bar, more preferably 10 to 30 bar.

In a preferred embodiment, the reaction is appropriately performed using the same diol, polyol or carbonate as a solvent. In an alternative embodiment, or in the case of use of solid glycols, the glycol can be diluted with an inert solvent or dissolved in an inert solvent. Suitable inert solvents are aliphatic, aromatic or halogenated hydrocarbons, ethers, esters or carbonates. Preferred solvents are chlorobenzene, dichlorobenzene, toluene, xylene, DMF, dimethylacetamide, tetrahydrofuran, NMP, DME, ethyl acetate, ethylene carbonate or propylene carbonate.

The reaction can be performed continuously or batchwise. In the preferred continuous mode of operation, the reaction gases are generally used in excess and the unconverted gas is circulated.

The redox catalyst used is at least one noble metal selected from palladium, rhodium, iridium and platinum in elemental form or the ionic or nonionic compounds thereof. The noble metal is preferably used as a compound soluble in the reaction mixture. Particularly suitable examples are the salts or the organometallic compounds of palladium in the II oxidation state, rhodium in the I or III oxidation state, iridium in the I or III oxidation state or platinum in the II oxidation state. However, the noble metals can also be used in another oxidation state and as supported or unsupported finely dispersed metal. Particular preference is given to using palladium as the noble metal, in which case it may be present either in elemental form or as a compound. When salts are used, anions suitable as counterions and all of those which are stable under reaction conditions and coordinate only weakly to the metal ion. Examples of such salts are the sulphates, sulphonates, chlorides, bromides, acetates and trichloroacetates of the above-mentioned noble metals.

The redox-active cocatalyst used is at least one compound selected from manganese compounds, cobalt compounds and copper compounds, in a weight ratio of catalyst compound to redox-active substance of 1:1 to 1:100, preferably 1:2 to 1:30. Examples of manganese compounds, cobalt compounds and copper compounds in the process according to the invention are the oxides, sulphates, halides, acetylacetonates or carboxylates thereof.

It is additionally possible to use a base, bromide sources, quaternary salts, various quinones or hydroquinones and desiccants. It is also possible for other redox-active substances, such as quinones, alkali metal or alkaline earth metal iodides, to be present in a weight ratio of catalyst compound to redox-active substance of 1:1 to 1:100, preferably 1:2 to 1:30. Examples of quinones are benzoquinone, naphthoquinone and anthraquinone, and the substitution products thereof.

Further assistants used may be onium salts such as ammonium, phosphonium or sulphonium salts, lead compounds such as lead alkyls or oxides, polymers such as polyvinylpyrrolidone, alkyl halides such as dibromoethane, in a weight ratio of catalyst compound to assistant of 1:1 to 1:10 000, preferably 1:10 to 1:1000. Particular preference is given to using potassium bromide or the bromides of the ammonium or phosphonium compounds in a weight ratio of catalyst compound to assistant of 1:1 to 1:10 000, preferably 1:10 to 1:1000.

Diaryl carbonates prepared in the context of the invention, in steps (h) and (i), are preferably those of the general formula (VII)

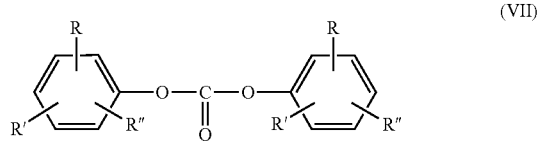

where R, R' and R" are each independently H, linear or branched, optionally substituted $C_1$-$C_{34}$-alkyl, preferably $C_1$-$C_6$-alkyl, more preferably $C_1$-$C_4$-alkyl, $C_1$-$C_{34}$-alkoxy, preferably $C_1$-$C_6$-alkoxy, more preferably $C_1$-$C_4$-alkoxy, $C_5$-$C_{34}$-cycloalkyl, $C_7$-$C_{34}$-alkylaryl, $C_6$-$C_{34}$-aryl or a halogen radical, preferably a chlorine radical, and R, R' and R" on both sides of the formula (VII) may be the same or different. R may also be —COO—R''' where R''' may be H, optionally branched $C_1$-$C_{34}$-alkyl, preferably $C_1$-$C_6$-alkyl, more preferably $C_1$-$C_4$-alkyl, $C_1$-$C_{34}$-alkoxy, preferably $C_1$-$C_6$-alkoxy, more preferably $C_1$-$C_4$-alkoxy, $C_5$-$C_{34}$-cycloalkyl, $C_7$-$C_{34}$-alkylaryl or $C_6$-$C_{34}$-aryl. Preferably, R, R' and R" on both sides of the formula (VII) are the same. Most preferably, R, R' and R" are each H.

Diaryl carbonates of the general formula (VII) are, for example: diphenyl carbonate, methylphenyl phenyl carbonates and di(methylphenyl)carbonates, also as a mixture, where the position of the methyl group on the phenyl rings may be as desired, and also dimethylphenyl phenyl carbonates and di(dimethylphenyl)carbonates, also as a mixture, where the position of the methyl groups on the phenyl rings may be as desired, chlorophenyl phenyl carbonates and di(chlorophenyl)carbonates, where the position of the methyl group on the phenyl rings may be as desired, 4-ethylphenyl phenyl carbonate, di(4-ethylphenyl)carbonate, 4-n-propylphenyl phenyl carbonate, di(4-n-propylphenyl)carbonate, 4-isopropylphenyl phenyl carbonate, di(4-isopropylphenyl) carbonate, 4-n-butylphenyl phenyl carbonate, di(4-n-butylphenyl)carbonate, 4-isobutylphenyl phenyl carbonate, di(4-isobutylphenyl)carbonate, 4-tert-butylphenyl phenyl carbonate, di(4-tert-butylphenyl)carbonate, 4-n-pentylphenyl phenyl carbonate, di(4-n-pentylphenyl)carbonate, 4-n-hexylphenyl phenyl carbonate, di(4-n-hexylphenyl)carbonate, 4-isooctylphenyl phenyl carbonate, di(4-isooctylphenyl) carbonate, 4-n-nonylphenyl phenyl carbonate, di(4-n-nonylphenyl)carbonate, 4-cyclohexylphenyl phenyl carbonate, di(4-cyclohexylphenyl)carbonate, 4-(1-methyl-1-phenylethyl)phenyl phenyl carbonate, di[4-(1-methyl-1-phenylethyl)phenyl]carbonate, biphenyl-4-yl phenyl carbonate, di(biphenyl-4-yl)carbonate, 1-naphthyl phenyl carbonate, 2-naphthyl phenyl carbonate, di(1-naphthyl)carbonate, di(2-naphthyl)carbonate, 4-(1-naphthyl)phenyl phenyl carbonate, 4-(2-naphthyl)phenyl phenyl carbonate, di[4-(1-naphthyl)phenyl]carbonate, di[4-(2-naphthyl)phenyl]carbonate, 4-phenoxyphenyl phenyl carbonate, di(4-phenoxyphenyl) carbonate, 3-pentadecylphenyl phenyl carbonate, di(3-pentadecylphenyl)carbonate, 4-tritylphenyl phenyl carbonate, di(4-tritylphenyl)carbonate, (methyl salicylate)phenyl carbonate, di(methyl salicylate)carbonate, (ethyl salicylate)phenyl carbonate, di(ethyl salicylate)carbonate, (n-propyl salicylate)phenyl carbonate, di(n-propyl salicylate)carbonate, (isopropyl salicylate)phenyl carbonate, di(isopropyl salicylate)carbonate, (n-butyl salicylate)phenyl carbonate, di(n-butyl salicylate)carbonate, (isobutyl salicylate)phenyl carbonate, di(isobutyl salicylate)carbonate, (tert-butyl salicylate) phenyl carbonate, di(tert-butyl salicylate)carbonate, di(phenyl salicylate)carbonate and di(benzyl salicylate)carbonate.

Preferred diaryl carbonates are: diphenyl carbonate, 4-tert-butylphenyl phenyl carbonate, di(4-tert-butylphenyl)carbonate, biphenyl-4-yl phenyl carbonate, di(biphenyl-4-yl)carbonate, 4-(1-methyl-1-phenyl ethyl)phenyl phenyl carbonate and di[4-(1-methyl-1-phenylethyl)phenyl]carbonate.

Particular preference is given to diphenyl carbonate.

In the process according to the invention, the aromatic hydroxyl compound(s) and the dialkyl carbonate(s) are used in the first reaction column preferably in a molar ratio of 1:0.1 to 1:10, more preferably of 1:0.2 to 1:5, most preferably of 1:0.5 to 1:3. The molar ratio specified does not take account of the recycling of aromatic hydroxyl compound or dialkyl carbonate into the reaction column via one or more top condenser(s) or one or more of any reboiler(s) present.

Aromatic hydroxyl compound(s) (monophenols) which are suitable in the context of the invention and are used in step (h) are preferably those of the general formula (VIII)

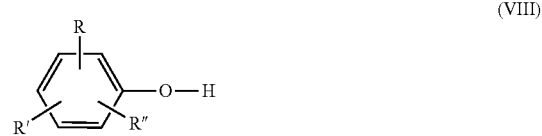

in which R, R' and R" may each independently be as defined for the general formula (VII).

Such aromatic monophenols are, for example: phenol, o-, m- or p-cresol, also as a mixture of the cresols, dimethylphenol, also as a mixture, where the position of the methyl groups on the phenol ring may be as desired, e.g. 2,4-, 2,6-, or 3,4-dimethylphenol, o-, m- or p-chlorophenol, o-, m- or p-ethylphenol, o-, m- or p-n-propylphenol, 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicylic acid, isopropylsalicylic acid, n-butylsalicylic acid, isobutylsalicylic acid, tert-butylsalicylic acid, phenylsalicylic acid and benzylsalicylic acid.

Preferred monophenols are phenol, 4-tert-butylphenol, biphenyl-4-ol and 4-(1-methyl-1-phenylethyl)phenol.

Particular preference is given to phenol.

Alkyl aryl carbonates obtained as intermediates in the context of the invention, in step (h), are preferably those of the general formula (IX)

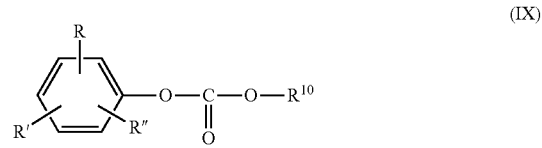

in which R, R' and R" may each be as defined for the general formula (VII), and $R^{10}$ as defined for the general formula (II).

Preferred alkyl aryl carbonates are methyl phenyl carbonate, ethyl phenyl carbonate, propyl phenyl carbonate, butyl phenyl carbonate, ethyl p-cresyl carbonate, methyl or ethyl p-chlorophenyl carbonate, hexyl phenyl carbonate, methyl o-cresyl carbonate, methyl p-cresyl carbonate, ethyl o-cresyl carbonate. Particularly preferred alkyl aryl carbonates are methyl phenyl carbonate, ethyl phenyl carbonate and butyl phenyl carbonate. Very particular preference is given to methyl phenyl carbonate and ethyl phenyl carbonate.

Catalysts for the transesterification of dialkyl carbonates and/or alkyl aryl carbonates with monophenols include alkali metal hydroxides, Lewis acids from the group of the metal halides (DE-A 2 528 412), organotin compounds (EP 879 A1, EP 880 A1, DE-A 3 445 552, EP 338 760 A1), lead compounds (JP 57/176 932), Lewis acid/protic acid catalysts (DE-A 3 445 553).

The process according to the invention for preparing diaryl carbonates in steps (h) and (i) is performed in at least two reaction columns.

Useful first and second reaction columns or any third or further column(s) include columns known to those skilled in the art. These are, for example, distillation and rectification columns, preferably reactive distillation and reactive rectification columns.

The first reaction column comprises at least one rectifying section in the upper part of the column and at least one reaction zone below the rectifying section which has at least two sectors. Each of the two sectors independently has preferably 0 to 20, preferably 0.1 to 20, theoretical plates each. In preferred embodiments, at least one rectifying section of the first reaction column is equipped with at least one intermediate condenser. The intermediate condenser is preferably mounted between the two sectors of the rectifying section. In this case, the rectifying section is divided into an upper rectifying section and a lower rectifying section.

The first reaction column is preferably operated in countercurrent, in which case the aromatic hydroxyl compound is preferably conducted in liquid form from the top to the bottom in at least one reaction zone of this column and the dialkyl carbonate is conducted counter to this liquid stream in gaseous form. The first reaction column is preferably operated in such a way that one or more streams comprising the aromatic hydroxyl compound and optionally dissolved transesterification catalyst are metered into at least one reaction zone, preferably into the upper third of the reaction zone, preferably with the temperature existing at this point in the column, in liquid form or with only a low gaseous content, the gaseous content preferably being less than 20% by weight. In addition, one or more streams comprising the dialkyl carbonate are passed into the reaction zone, preferably in the lower third of this reaction zone, the metered addition preferably being effected in gaseous or superheated form. In preferred embodiments, the superheating of the vapour stream may be 0 to 50° C. In addition, the dew point temperature is preferably guided by the pressure which exists in the reaction zone at the metering point of the particular stream comprising dialkyl carbonate.

After passing through the reaction zone(s), the alkyl alcohol formed during the reaction, after passing through the rectifying section(s), is withdrawn at the top of the first reaction column. The alkyl alcohol formed during the reaction, also known as alcohol of reaction, in the context of the invention, is the alcohol released in the course of transesterification, preferably $R^1$—OH and/or $R^2$—OH, where $R^1$ and $R^2$ are each defined as specified for the general formula (II). The stream withdrawn at the top of the first reaction column generally comprises, in addition to the alkyl alcohol formed during the reaction, excess or unconverted dialkyl carbonate and low-boiling secondary compounds, for example carbon dioxide or dialkyl ether. Owing to the rectifying section(s) present, this stream comprises only small amounts of higher-boiling components, for example the aromatic hydroxyl compound. The rectifying section serves to remove the higher-boiling components which are also evaporated in the reaction zone, for example the aromatic hydroxyl compound or alkyl aryl carbonate, from the low-boiling alcohols of reaction or dialkyl carbonates. This has the advantage that the separation of the alkyl alcohols formed during the reaction from the dialkyl carbonates can be performed at a low temperature level.

In preferred embodiments, the first reaction column is operated under reflux conditions. "Reflux conditions" is understood to mean a method in which the vapour stream is condensed fully or partly at the upper end of the rectifying section and the condensate obtained is recycled partly or fully as reflux back to the upper end of the rectifying section. The return ratio is preferably 0.1 to 20, more preferably 0.1 to 10 and most preferably 0.1 to 3, the return ratio in the context of the invention corresponding to the weight ratio of condensate recycled into the column to vapour withdrawn at the top of the column without recycled condensate.

In preferred embodiments, the first reaction column has at least one stripping section below a reaction zone.

The first reaction column may further preferably be equipped with one or more reboiler(s). When the first reaction column is designed with a stripping section, preference is given to additionally using a reboiler which fully or partly evaporates the liquid effluxing from the stripping section. This fully or partially evaporated liquid stream is recycled fully or partly back into the first reaction column. In the case of an embodiment without a stripping section, in any reboiler used, the liquid effluxing from the reaction zone is evaporated fully or partly and recycled fully or partly back into the first reaction column.

Additionally preferably, the first reaction column may have one or more intermediate heaters or intermediate vaporizers in the region of the stripping section and/or of the reaction zone.

In the preferred embodiments in which at least one rectifying section of the first reaction column is equipped with at least one intermediate condenser, the rectifying section of the first reaction column, which is equipped with at least one intermediate condenser, is divided into a lower rectifying section and an upper rectifying section (two sectors), of which the lower rectifying section is present below the intermediate condenser and the upper rectifying section above the intermediate condenser.

The rectifying section(s) with at least one intermediate condenser may, in preferred embodiments, be accommodated in the reaction column together with the reaction section(s) and optionally at least one stripping section. In this case, the vaporous mixture coming from the reaction zone(s) is passed from below into a lower sector of the rectifying section and/or if appropriate into the lower rectifying section, which depletes the aromatic hydroxyl compound. The vaporous mixture coming from this lower sector or if appropriate the lower rectifying section is passed into an intermediate condenser, where it partly condenses out, and the condensate obtained is fed in at the upper end of the lower sector of the rectifying section or if appropriate to the lower rectifying section.

In a further preferred embodiment of the process according to the invention, the intermediate condenser is not integrated into the first reaction column, but configured as a separate intermediate condenser outside the first reaction column.

In a further preferred embodiment of the process according to the invention, intermediate condenser and the upper sector of the rectifying section are not integrated into the reaction column but accommodated separately outside the first reaction column.

Below the reaction zone and any stripping section present, a mixture comprising alkyl aryl carbonate, excess or unconverted phenol, diaryl carbonate, transesterification catalysts, dialkyl carbonate, alcohol of reaction and high-boiling compounds which form in the reaction or are already present in the reactants is obtained. When a stripping section is used, the content of low-boiling compounds, for example dialkyl carbonate and alcohol of reaction, is reduced, forming further alkyl aryl carbonate and/or diaryl carbonate under some circumstances in the presence of the transesterification catalyst. The energy required for this purpose is preferably supplied by one or more vaporizers.

In all sections of the first reaction column and also of the columns described hereinafter, i.e. both in rectifying and/or any stripping section and/or in the reaction zone, random packings or structured packings can be used to achieve the separating performance in question. The random packings or structured packings for use are those customary for distillations, as described, for example, in Ullmann's Encyclopädie der Technischen Chemie, 4th ed., vol. 2, p. 528 ff. Examples of random packings include Raschig or Pall and Novalox rings, Berl, Intalex or Torus saddles, Interpack bodies, and examples of structured packings include sheet metal and fabric packings (for example BX packings, Montz Pak, Mellapak, Melladur, Kerapak and CY packing) made of various materials, such as glass, stoneware, porcelain, stainless steel, plastic. Preference is given to random packings and structured packings which have a large surface area, good wetting and sufficient residence time of the liquid phase. These are, for example, Pall and Novalox rings, Berl saddles, BX packings, Montz Pak, Mellapak, Melladur, Kerapak and CY packings.

In the context of the invention, a "sector" is notable in that a feed and/or withdrawal point is present below and/or above this sector. In the case of use of random packings and/or structured packings, a sector can be divided into a plurality of parts when the sector has more than 4, preferably more than 10 and more preferably more than 15 theoretical plates.

Alternatively suitable are also column trays, for example sieve trays, bubble-cap trays, valve trays, tunnel-cap trays. In the reaction zone(s) of the reaction column, particular preference is given to column trays with high residence times coupled with good mass transfer, for example bubble-cap trays, valve trays or tunnel-cap trays with high overflow weirs.

The number of theoretical plates of the reaction zone of the first reaction column is preferably 3 to 50, more preferably 10 to 50 and most preferably 10 to 40. The liquid holdup is preferably 1 to 80%, more preferably 5 to 70% and most preferably 7 to 60% of the internal column volume of the reaction zone. The more exact design of the reaction zone(s), of any stripping section to be used and of the rectifying section(s) can be undertaken by the person skilled in the art.

In the first reaction column, the column diameter in the region of the reaction zone is guided by the gas throughput, but only with restrictions. It is also influenced by the holdup to be achieved.

In the case of use of delay trays, the liquid level on the trays should preferably be 50 to 1000, more preferably 100 to 500 and most preferably 100 to 250 mm in order to limit the pressure drop of the column to a sensible level. The pressure drop of the column should preferably be less than 50, more preferably less than 30 and most preferably less than 25% of the top pressure.

Under these boundary conditions, the F factor in the column is preferably between 0.05 and 2.5, preferably 0.05 to 1.5 and more preferably between 0.08 and 1 $Pa^{0.5}$. The tray separation may preferably be 250 to 1500 mm, more preferably 300 to 1000 and most preferably 500 to 1000 mm The F factor is a measure of the gaseous hydrodynamic loading of the column and is calculated as follows:

$$F \text{ factor} = \text{gas density}^{1/2} \times \text{gas velocity}$$

A suitable column design of the rest of the distillation and/or reaction columns used in the process, which includes the design of the column height and of the column diameter, the selection of the column internals and the dimensioning of the feed and withdrawal lines, is known to those skilled in the art and can be taken from the relevant literature (for example Distillation Design, Henry Z. Kister, McGraw Hill; Distillation Operation, Henry Z. Kister, McGraw Hill; Perry's Chemical Engineering Handbook; Perry & Green).

The temperature of the reaction zone(s) is preferably in the range from 100 to 300° C., more preferably from 120 to 250° C., most preferably from 150 to 240° C. In preferred embodiments, an optimal reaction temperature is established in the reaction zone firstly through the selection of the operating conditions and secondly through additional heat supply in the region of one or more reaction trays. The heat can be supplied to the reaction trays either by means of heat exchangers or via reaction trays with means of introducing heat. It is advantageous to perform the inventive transesterification not only at atmospheric pressure, but also at elevated or reduced pressure. The pressure in the reaction zone is therefore preferably in the range of 0.5 to 20 bar (absolute), more preferably 0.8 to 15 bar (absolute), most preferably 0.9 to 10 bar (absolute).

For the reaction steps which occur in the first reaction column, it is possible to use transesterification catalysts known from the literature. These are transesterification catalysts known from the literature for the dialkyl carbonate-phenol transesterification, such as $AlX_3$, $TiX_3$, $UX_4$, $TiX_4$, $VOX_3$, $VX_5$, $ZnX_2$, $FeX_3$, $PbX_2$ and $SnX_4$, in which X represents halogen, acetoxy, alkoxy or aryloxy radicals (DE-A 2 58 412). Particularly preferred catalysts usable in accordance with the invention are metal compounds such as $AlX_3$, $TiX_4$, $PbX_2$ and $SnX_4$, for example titanium tetrachloride, titanium tetramethoxide, titanium tetraphenoxide, titanium tetraethoxide, titanium tetraisopropoxide, titanium tetradodecoxide, tin tetraisooctoxide and aluminum triisopropoxide. Very particular preference is given to metal compounds $TiX_4$. The metal compounds mentioned are used preferably in amounts of 0.001 to 5% by weight, preferably of 0.005 to 5% by weight and more preferably of 0.01 to 5% by weight, based on the weight of the reaction mixture to be converted.

In the context of the invention, halogen is fluorine, chlorine or bromine, preferably fluorine or chlorine, more preferably chlorine.

Further catalysts usable in accordance with the invention are organotin compounds of the general formula $(R^{11})_{4-x}$—$Sn(Y)_x$ in which Y is an $OCOR^{12}$, OH or OR radical, where $R^{12}$ is $C_1$-$C_{12}$-alkyl, $C_6$-$C_{12}$-aryl or $C_7$-$C_{13}$-alkylaryl, $R^{11}$ is as defined for $R^{12}$ independently of $R^{12}$, and x is an integer from 1 to 3, dialkyltin compounds having 1 to 12 carbon atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctoxide, octyltin triisooctoxide, butylstannoic acid and octylstannoic acid, in amounts of 0.001 to 20% by weight (cf. EP 879, EP 880, EP 39 452, DE-A 34 45 555, JP 79/63023), polymeric tin compounds of the formula —[—RR$^{11}$Sn—O—]— in which R and R$^{11}$ are each independently as defined above for R$^{12}$, for example poly[oxy(dibutylstannylene)], poly[oxy(dioctylstannylene)], poly[oxy(butylphenylstannylene)], and poly[oxy(diphenylstannylene)] (DE-A 34 45 552), polymeric hydroxystannoxanes of the formula —[—RSn(OH)—O—]—, for example poly(ethylhydroxystannoxane), poly(butylhydroxystannoxane), poly(octylhydroxystannoxane), poly(undecylhydroxystannoxane) and poly(dodecylhydroxystannoxane), in amounts of 0.001 to 20% by weight, preferably of 0.005 to 5% by weight, based on dialkyl carbonate (DE-A 40 06 520). Further tin compounds usable in accordance with the invention are Sn(II) oxides of the general formula

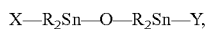

X—R$_2$Sn—O—R$_2$Sn—Y, in which X and Y are each independently OH, SCN, OR$^{13}$, OCOR$^{13}$ or halogen and R is alkyl, aryl, in which R$^{13}$ is as defined above for R$^{12}$ (EP 0 338 760).

Further catalysts usable in accordance with the invention include lead compounds, optionally together with triorganophosphanes, a chelate compound or an alkali metal halide, for example Pb(OH)$_2$-2PbCO$_3$, Pb(OCO—CH$_3$)$_2$, Pb(OCO—CH$_3$)$_2$.2LiCl, Pb(OCO—CH$_3$)$_2$.2PPh$_3$ in amounts of 0.001 to 1 and preferably of 0.005 to 0.25 mol per mole of dialkyl carbonate (JP 57/176932, JP 01/093580), and other lead(II) and lead(IV) compounds, such as PbO, PbO$_2$, minium, plumbites and plumbates (JP 01/093560), iron(III) acetate (JP 61/1 72 852), and also copper salts and/or metal complexes, for example of alkali metal, zinc, titanium and iron (JP 89/005588).

In addition, heterogeneous catalyst systems are usable in the processes according to the invention. These are, for example, mixed oxides of silicon and titanium, which are obtainable by combined hydrolysis of silicon and titanium halides (JP 54/125617), or titanium dioxides with a high BET surface area of >20 m$^2$/g (DE-A 40 36 594).

Preferred catalysts for the process according to the invention are the above-specified metal compounds AlX$_3$, TiX$_3$, UX$_4$, TiX$_4$, VOX$_3$, VX$_5$, ZnX$_2$, FeX$_3$, PbX$_2$ and SnX$_4$. Particular preference is given to AlX$_3$, TiX$_4$, PbX$_2$ and SnX$_4$, among which mention should be made by way of example of titanium tetrachloride, titanium tetramethoxide, titanium tetraphenoxide, titanium tetraethoxide, titanium tetraisopropoxide, titanium tetradodecoxide, tin tetraisooctoxide and aluminum triisopropoxide. Very particular preference is given to metal compounds TiX$_4$. Especially preferred are titanium tetramethoxide, titanium tetraphenoxide and titanium tetraethoxide.

The catalyst is preferably introduced into the first reaction column in dissolved or suspended form together with the stream comprising the aromatic hydroxyl compound(s). Alternatively, the catalyst can also be metered in separately, for example, in an alcohol corresponding to the alcohol of reaction or a suitable inert solvent. In the case of use of heterogeneous catalysts, they can be used in a mixture with the random packings mentioned, in a suitable shape in place of random packings or as a bed on any column trays installed.

The energy required for the reaction in the first reaction column can firstly be generated by means of internal or external apparatus, for example heat exchangers, vaporizers and/or heatable column trays, and/or secondly introduced either with the liquid stream comprising the aromatic hydroxyl compound(s) or with the stream which comprises dialkyl carbonate and is metered in gaseous form. Especially in the region of the reaction zone(s), heat can be supplied in this way. This heat is preferably supplied in the region of the reaction zone(s) fully or partly by means of vaporizers or heatable column trays. It is particularly advantageous to introduce the energy required for the reaction in the first reaction column into the first reaction column at least partly either with the liquid stream comprising the aromatic hydroxyl compound(s) or with the stream which comprises dialkyl carbonate and is metered in gaseous form, and additionally by means of internal and/or external heat exchangers.

In the process according to the invention, the bottom product of the first reaction column is fed to a second reaction column.

The second reaction column comprises at least one rectifying section in the upper part of the column and at least one reaction zone below the rectifying section. The rectifying section has preferably 1 to 50 and more preferably 1 to 25 theoretical plates.

In the second reaction column, the bottom product of the first reaction column, which already comprises alkyl aryl carbonate and diaryl carbonate formed, is fed in liquid form or as a vapour-liquid mixture, preferably to the reaction zone, more preferably to the upper part of the reaction zone, most preferably in the upper third of the reaction zone. In this case, the second reaction column is preferably operated such that the alkyl aryl carbonate is converted partly or fully, for example by further transesterification or disproportionation, preferably by disproportionation, to the diaryl carbonate. In addition to the bottom product of the first reaction column, it is possible to meter in one or more streams comprising alkyl aryl carbonate in the region of the reaction zone in liquid form or as a vapour-liquid mixture. Such additional streams comprising alkyl aryl carbonate may originate, for example, from the further workup and be recycled thus into the process.

At the top of the second reaction column, unconverted aromatic hydroxyl compound, dialkyl carbonate, alcohol of reaction, medium-boiling secondary compounds—for example alkyl aryl ethers—and, to a minor degree, low-boiling secondary compounds are removed. In the context of the invention, medium-boiling secondary compounds are understood to mean those having a boiling point below that of the alkyl aryl carbonate and above that of the dialkyl carbonate. Such medium-boiling secondary compounds are, for example, alkyl aryl ethers, for example anisole or phenetole. The medium-boiling secondary compounds removed in the second reaction column may form in the reaction in the first and/or second reaction column or already have been introduced into the process through the reactants.

The rectifying section of the second reaction column serves to remove the higher-boiling components also evaporated in the reaction zone, for example alkyl aryl carbonate.

In preferred embodiments, the second reaction column is likewise operated under those reflux conditions described for the first reaction column.

The second reaction column may have at least one stripping section below a reaction zone. In preferred embodiments, the reaction zone of the second reaction column may, however, function simultaneously as a stripping section. In this case, the dialkyl carbonate released in the disproportionation is removed by transesterification of alcohol of reaction released and unconverted aromatic hydroxyl compound, and diaryl carbonate and the alkyl aryl carbonate which is depleted essentially through disproportionation are simultaneously concentrated.

The second reaction column may additionally preferably be equipped with one or more reboiler(s).

Additionally preferably, the second reaction column may have, in the region of the stripping section and/or of the reaction zone, one or more intermediate heaters or intermediate vaporizers.

In principle, the rectifying section of the second reaction column may likewise be equipped with one or more intermediate condensers. This divides the rectifying section into a lower rectifying section and an upper rectifying section (two sectors), of which the lower rectifying section is present below the intermediate condenser and the upper rectifying section above the intermediate condenser. In a preferred embodiment, the second reaction column does not have an intermediate condenser.

The second reaction column is equipped with one or more condensers. These are preferably one or more condensers at the top of the second reaction column (top condenser(s)). Particular preference is given to using a cascade of top condensers.

In the course of the condensation in the condenser(s) at the top of the second reaction column, the vapours become depleted in relatively high-boiling components, for example aromatic hydroxyl compound. In order to be able to particularly efficiently utilize the heat of condensation obtained for the purposes of thermal integration, the condensation is therefore preferably effected in several stages, more preferably at least two stages, and in preferred embodiments in two or three stages.

In the particularly preferred embodiment of two- or three-stage condensation, the heat of condensation of the first or of the first and second condensation stage is used directly or indirectly to heat a stream or a column within the process, while the heat of condensation obtained from the second or third condensation stage is removed by cooling water or air cooling.

The condensation at the top of the second reaction column can, in further preferred embodiments, additionally be carried out by not condensing a portion of the vapours withdrawn at the top of the second reaction column, in order to be able to selectively discharge medium-boiling secondary compounds.

Below the reaction zone and any stripping section present, a mixture comprising alkyl aryl carbonate, excess or unconverted aromatic hydroxyl compound, diaryl carbonate, transesterification catalyst(s), dialkyl carbonate, alcohol of reaction and medium- or high-boiling secondary compounds formed in the reaction or already present in the reactants is obtained. In the context of the invention, high-boiling secondary compounds are understood to mean those having a boiling point above that of the alkyl aryl carbonate. Such high-boiling secondary compounds can be divided into those whose boiling point is between that of the alkyl aryl carbonate and that of the diaryl carbonate (high boilers), and those whose boiling point is above the boiling point of the diaryl carbonate (very high boilers).

In all sections of the second reaction column, i.e. both in the rectifying section and any stripping section, and in the reaction zone, the random packings or structured packings already cited above for the first reaction column can be used.

The more exact design of the reaction zone(s), of any stripping section to be used and of the rectifying section(s) can be undertaken by the person skilled in the art.

The temperature of the reaction zone(s) is preferably in the range of 100 to 300° C., more preferably of 120 to 250° C., most preferably of 180 to 250° C.

In particular embodiments, an optimal reaction temperature is established in the reaction zone firstly through the selection of the operating conditions and secondly through additional supply of heat in the region of one or more reaction trays. The heat can be supplied to the reaction trays either by means of heat exchangers or via reaction trays with means of introducing heat. It is advantageous to perform the inventive transesterification not only at standard pressure, but also under elevated or reduced pressure, preferably under reduced pressure. The pressure of the second reaction column is therefore preferably in the range from 0.05 to 20 bar (absolute), more preferably from 0.1 to 10 bar (absolute), most preferably from 0.1 to 2 bar (absolute).

For the reaction steps which occur in the second reaction column, the transesterification catalysts already cited above for the transesterification in the first reaction column can be used. In a preferred embodiment, identical catalysts are used in the first and second reaction columns.

The catalyst is preferably introduced into the second reaction column in dissolved or suspended form together with the bottom product of the first reaction column. Alternatively, the catalyst can also be metered in separately, for example, in an alcohol corresponding to the alcohol of reaction or a suitable inert solvent. In the case of use of heterogeneous catalysts, they can be used in a mixture with the random packings mentioned, in a suitable shape in place of random packings or as a bed on any column trays installed.

In the process according to the invention, in the course of transesterification and/or disproportionation in the first reaction column and/or the further reaction column(s), streams comprising alkyl alcohol formed during the reaction (alcohol of reaction) and dialkyl carbonate unconverted or formed during the reaction are obtained and are preferably withdrawn in a mixture in one or more streams. This dialkyl carbonate unconverted in the reaction columns or formed during the reaction is, according to the invention, separated fully or partly in at least one further process step comprising at least one distillation column from the alkyl alcohol formed during the reaction (alcohol of reaction). Preference is given to withdrawing at least one stream comprising dialkyl carbonate unconverted or formed during the reaction and alkyl alcohol formed during the reaction at the top of the first reaction column and separating it by feeding it to at least one further process step comprising at least one distillation column.

Preference is given to feeding the vapour mixture which is withdrawn at the top of the first reaction column and comprises dialkyl carbonate and alkyl alcohol formed during the reaction, after condensation at the top of the first reaction column, fully or partly to at least one further process step comprising at least one distillation column, for separation of dialkyl carbonate and alkyl alcohol—referred to hereinafter as separating distillation column(s). Particular preference is given to feeding the dialkyl carbonate removed, optionally after further purification, back to the first reaction column.

The dialkyl carbonate and the alcohol of reaction are preferably separated by distillation in one or more separating distillation columns or in a combination of distillation and membrane separation—referred to hereinafter as a hybrid process.

When alcohol of reaction and dialkyl carbonate form an azeotrope (e.g. methanol and dimethyl carbonate), preference is given to using an at least two-stage process, for example a two-pressure process, an extractive distillation, a heteroazeotrope distillation with a low-boiling azeotroping agent, or a hybrid process. Particular preference is given to employing the two-pressure process or a hybrid process. Very particular preference is given to employing the two-pressure process. Such processes are known in principle to those skilled in the art.

When alcohol of reaction and dialkyl carbonate do not form an azeotrope (e.g. ethanol and diethyl carbonate), the separation is preferably effected in a single separating distillation column.

When alcohol of reaction and dialkyl carbonate form an azeotrope, the distillate of a first separating distillation column of the process step for separating dialkyl carbonate and alkyl alcohol (alcohol of reaction) preferably has virtually azeotropic composition. In this case, it is preferably fed, in a two-pressure process, to at least one further separating distillation column which operates at an operating pressure below that of the first separating distillation column. As a result of the different operating pressure, the position of the azeotrope shifts toward lower proportions of alcohol of reaction. The bottom product obtained from this second separating distillation column or these further separating distillation column(s) is alcohol of reaction in a purity of 90 to 100% by weight, based on the total weight of the isolated bottom product, and the distillate obtained is a virtually azeotropic mixture. The second separating distillation column or further separating distillation column(s) which work at lower operating pressure is/are, in very particularly preferred embodiments, preferably operated with the heat of condensation of the top condenser(s) of the first separating distillation column.

The two-pressure process makes use of the pressure dependence of the azeotropic composition of a two-substance mixture. In the case of a mixture of alcohol of reaction (alkyl alcohol) and dialkyl carbonate, for example methanol and dimethyl carbonate, the azeotropic composition shifts to higher alcohol of reaction contents with increasing pressure. When a mixture of these two components is fed to a first separating distillation column (dialkyl carbonate column), the alcohol of reaction content being below the corresponding azeotropic composition for the operating pressure of this column, the distillate obtained is a mixture with virtually azeotropic composition and the bottom product virtually pure dialkyl carbonate. The azeotropic mixture thus obtained is fed to a further separating distillation column (alkyl alcohol column). This works at a lower operating pressure compared to the dialkyl carbonate column. As a result, the position of the azeotrope is shifted toward lower alcohol of reaction contents. This makes it possible to separate the azeotropic mixture obtained in the dialkyl carbonate column into a distillate with virtually azeotropic composition and virtually pure alcohol of reaction. The distillate of the alkyl alcohol column is fed back to the dialkyl carbonate column at a suitable point.

By the process according to the invention, it is preferably possible to obtain diaryl carbonates having a purity of, i.e. a content of pure diaryl carbonate of, 99 to 100% by weight, more preferably 99.5 to 100% by weight and most preferably 99.9 to 100% by weight, based on the total weight of the purified diaryl carbonate.

The diaryl carbonate withdrawn in the sidestream of the first diaryl carbonate distillation column can be withdrawn in liquid or vaporous form. The diaryl carbonate withdrawn in the sidestream of the first diaryl carbonate distillation column is preferably withdrawn in vaporous form. In preferred embodiments, however, liquid withdrawal of the diaryl carbonate in the sidestream may be preferred, more particularly owing to construction reasons.

Dividing wall columns are known to those skilled in the art and are described, for example, in DE-A 33 02 525 or DE-A 199 14 966.

In process step (f) a catalyst-containing stream is obtained and is recycled fully or partly, optionally after further purification, back into the process, preferably into process step (e). This allows both losses of expensive catalysts and losses of desired diaryl carbonate to be avoided and hence the process according to the invention additionally to be configured more economically viably.

FIG. 1 shows an integrated process for preparing polycarbonate and recycling of the ethylene glycol obtained and of the phenol.

Figure 2:
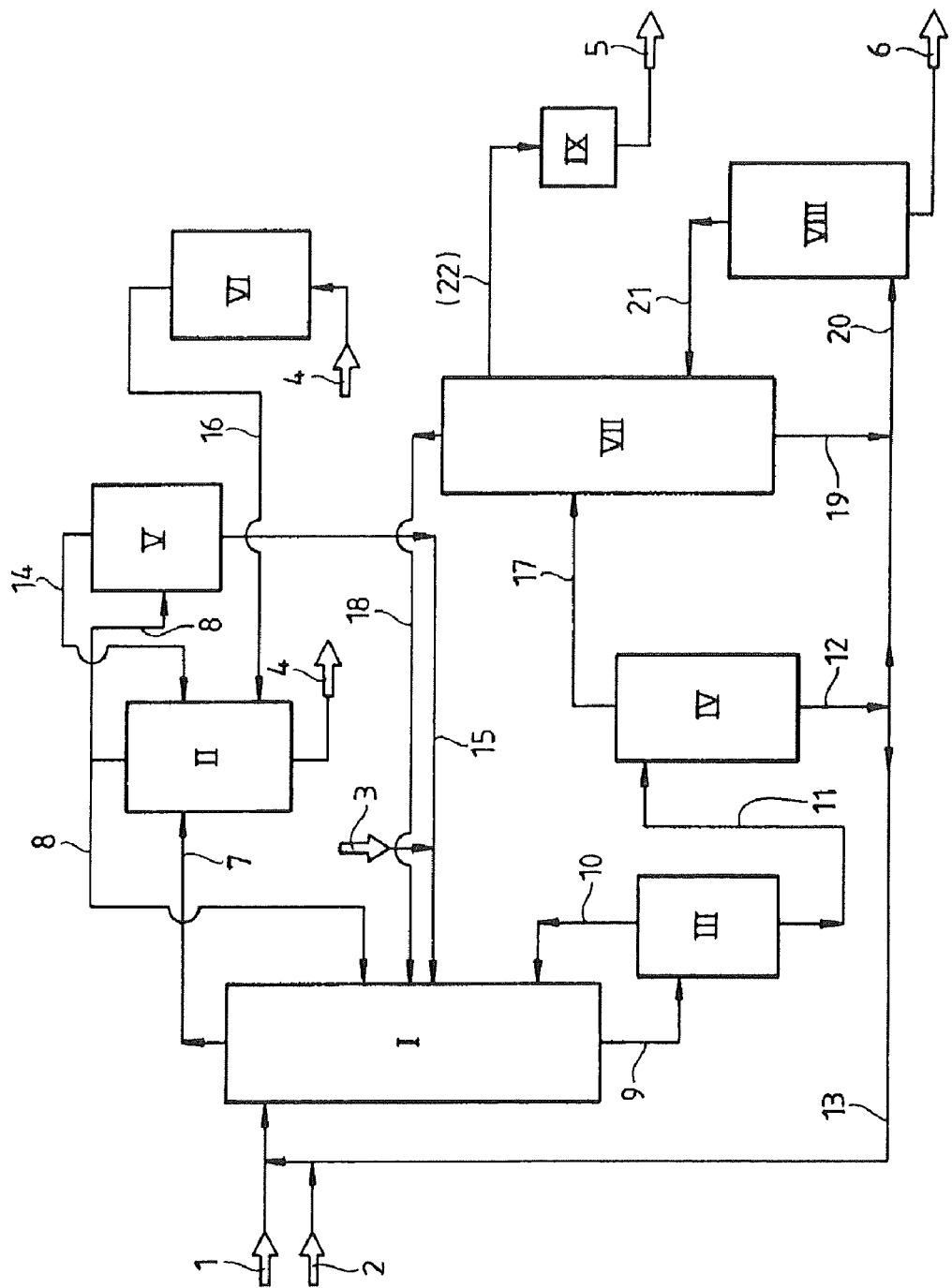
FIG. 2 shows one embodiment of the process for preparing dialkyl carbonate from alkylene carbonate.

FIG. 2 shows one embodiment of the process for preparing dialkyl carbonate from alkylene carbonate.

Figure 3:
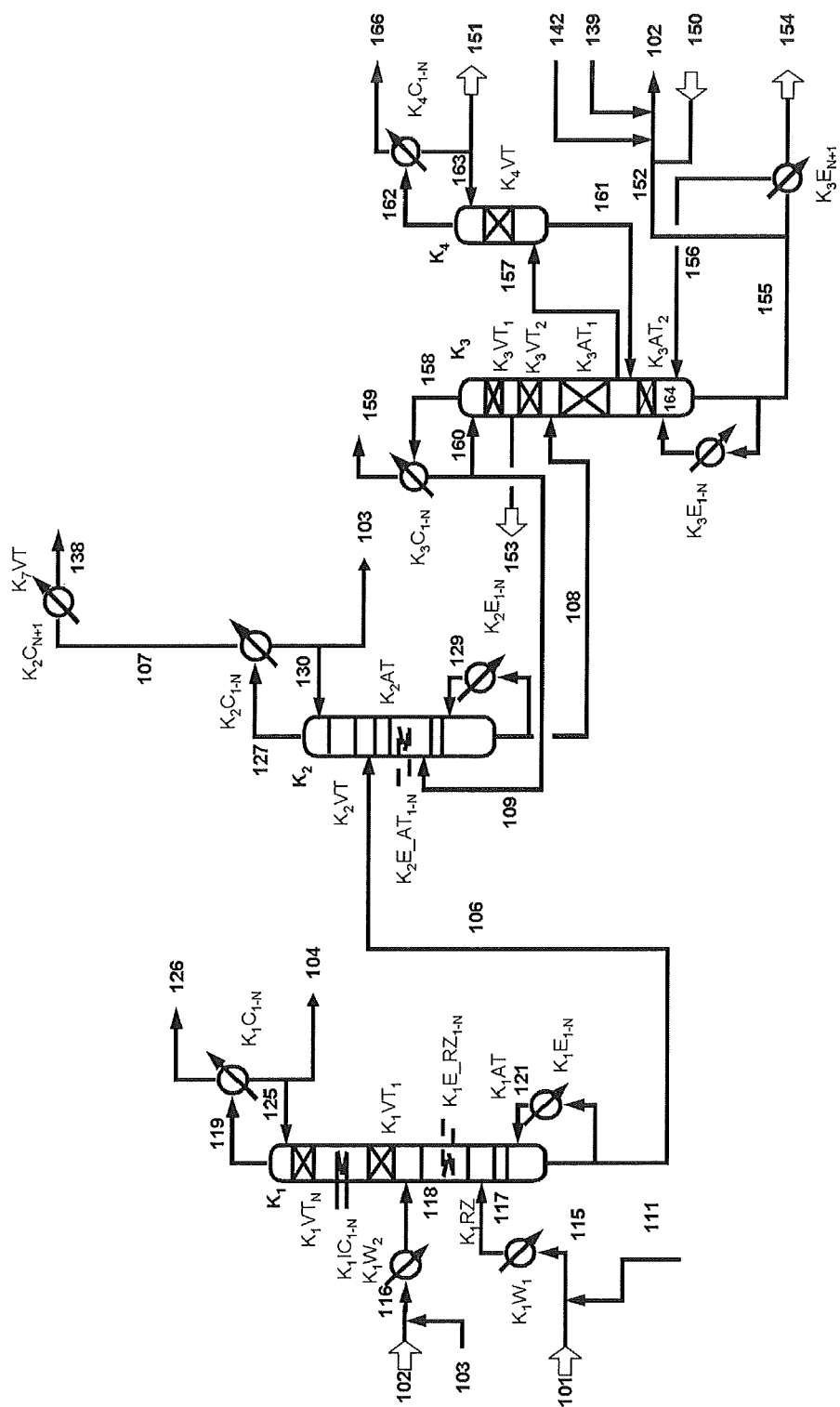
FIG. 3 shows one embodiment of the process for preparing diaryl carbonate from dialkyl carbonate.

FIG. 3 describes one embodiment of the process for preparing diaryl carbonate from dialkyl carbonate.

Figure 4:
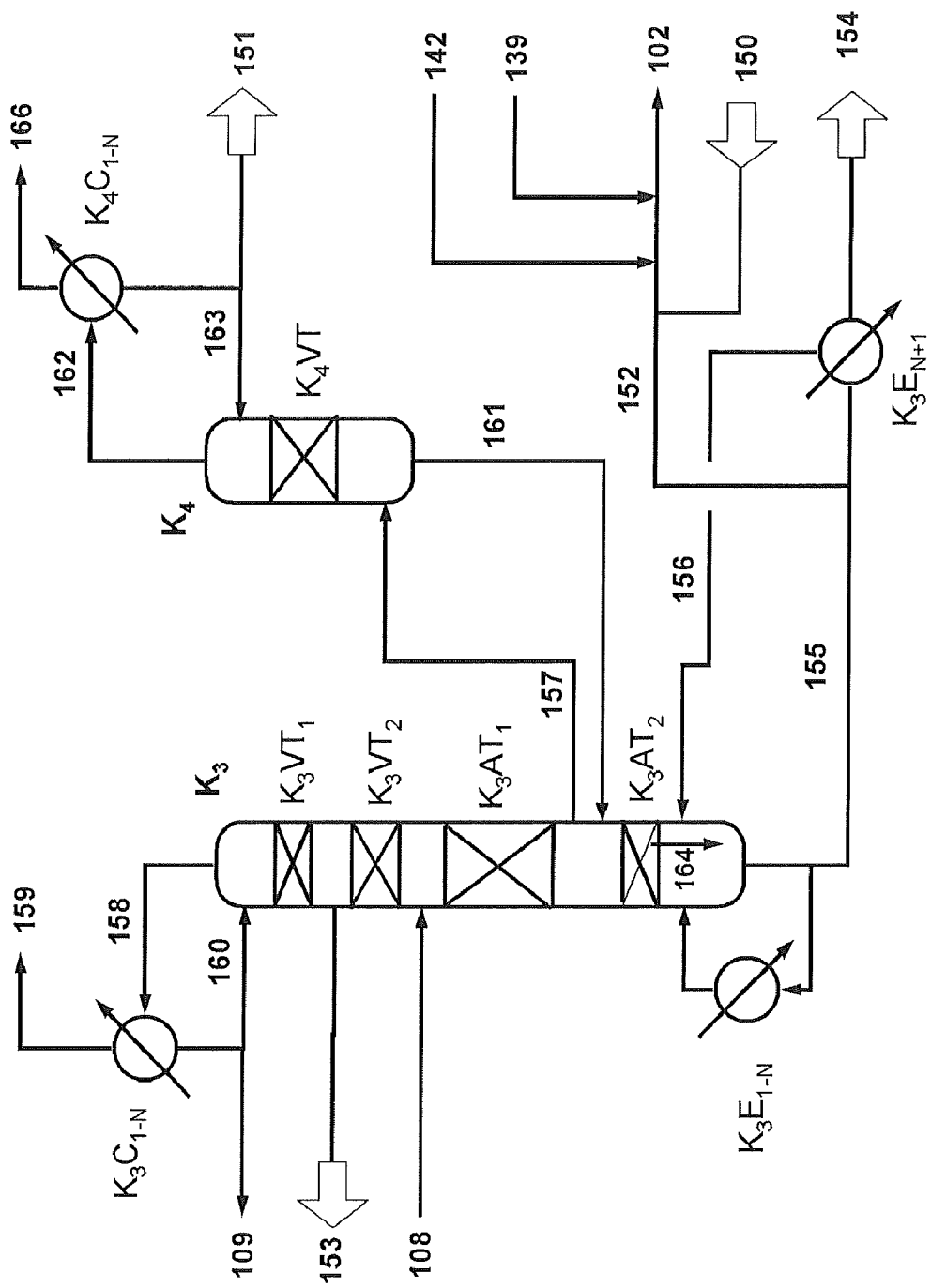
FIG. 4 shows one embodiment of the distillation of diaryl carbonate.

FIG. 4 describes one embodiment of the distillation of diaryl carbonate.

In FIG. 3 and FIG. 4, the reference numerals are each defined as follows:

$K_1$ alkyl aryl carbonate reaction column (first reaction column)
$K_1C_{1-N}$ top condenser(s) 1 to N of $K_1$
$K_1E_{1-N}$ vaporizer 1 to N of $K_1$
$K_1IC_{1-N}$ intermediate condenser(s) 1 to N of $K_1$
$K_1VT_1$ lower rectifying section of $K_1$
$K_1VT_N$ upper rectifying section of $K_1$
$K_1W_1$ preheater/vaporizer/superheater of $K_1$ for dialkyl carbonate-containing stream
$K_1W_2$ preheater/vaporizer of $K_1$ for reactant stream comprising aromatic hydroxyl compound
$K_1RZ$ reaction zone of $K_1$
$K_1AT$ stripping section of $K_1$
$K_1E\_RZ_{1-N}$ intermediate vaporizers 1 to N in the region of the reaction zone of $K_1$
$K_2$ diaryl carbonate reaction column (second reaction column)
$K_2C_{1-N}$ top condenser(s) 1 to N of $K_2$
$K_2C_{N+1}$ condenser for residual vapour stream from $K_2C_{1-N}$ containing medium-boiling secondary compounds
$K_2E_{1-N}$ vaporizers 1 to N of $K_2$
$K_2VT$ rectifying section of $K_2$
$K_2AT$ stripping section and reaction zone of $K_2$
$K_2E\_AT_{1-N}$ intermediate vaporizers 1-N in the stripping section of $K_2$
$K_3$ diaryl carbonate fine distillation column (first diaryl carbonate distillation column)
$K_3C_{1-N}$ optional multistage top condenser(s) 1 to N of $K_3$
$K_3E_{1-N}$ optional multistage vaporizer(s) 1 to N of $K_3$
$K_3E_{N+1}$ additional vaporizer for concentration of the bottom product stream which has not been recycled into the process from the bottom of column $K_3$ and/or of the column vaporizer(s) $K_3E_{1-N}$
$K_3SC_{1-N}$ optional multistage condenser(s) 1 to N for vaporous sidestream of $K_3$
$K_3VT_1$ upper rectifying section of $K_3$
$K_3VT_2$ lower rectifying section of $K_3$
$K_3AT_1$ upper stripping section of $K_3$
$K_3AT_2$ lower stripping section of $K_3$
$K_3T$ dividing wall of $K_3$
$K_3TLO$ rectifying section on the feed side of the dividing wall of $K_3$
$K_3TLU$ stripping section on the feed side of the dividing wall of $K_3$
$K_3TRU$ rectifying section on the withdrawal side of the dividing wall of $K_3$ K₃TRO stripping section on the withdrawal side of the dividing wall of K₃

K₄ diaryl carbonate sidestream column (second diaryl carbonate distillation column)

$K_4C_{1-N}$ optional multistage top condenser(s) 1 to N of K₄

K₄VT rectifying section of K₄

K₄AT stripping section of K₄

$K_4E_{1-N}$ optional multistage vaporizer(s) 1 to N of K₄

Additionally named in FIGS. 3 to 4 are the following streams:

101 reactant feed stream comprising dialkyl carbonate
102 reactant feed stream comprising aromatic hydroxyl compound
103 distillate of K2
104 distillate of K1
105 stream comprising dialkyl carbonate and alcohol of reaction
106 bottom product of K1
107 intermediate boiler purge
108 bottom product of K2
109 stream comprising alkyl aryl carbonate and aromatic hydroxyl compound
111 stream comprising dialkyl carbonate
115 dialkyl carbonate-containing stream to K1
116 aromatic hydroxyl compound-containing stream to K1
117 dialkyl carbonate-containing stream after evaporation
118 stream comprising aromatic hydroxyl compound after heating
119 vapour stream at the top of K1
120 liquid effluent from the stripping section of K1
121 vapour-liquid mixture from reboiler of K1
122 vapour mixture from lower rectifying section of K1
123 condensate of the intermediate condenser(s) of K1
124 efflux of liquid mixture from upper rectifying section of K1
125 return stream of K1
126 remaining vapour mixture from condensation of K1
127 vapour stream at the top of K1
128 efflux of liquid mixture from reaction zone or if appropriate stripping section of K2
129 vapour-liquid mixture from reboiler of K2
130 return stream of K2
138 stream comprising medium-boiling secondary compounds
150 stream comprising aromatic hydroxyl compound and catalyst
151 stream comprising diaryl carbonate with high purity
152 stream comprising high-boiling secondary compounds and catalyst
153 stream comprising medium-boiling secondary compounds
154 stream comprising high-boiling secondary compounds and catalyst for disposal
155 stream comprising high-boiling secondary compounds and catalyst
156 vapour stream comprising diaryl carbonate to K3
157 vapour stream comprising diaryl carbonate to K4
158 vapour stream of K3
159 residual vapour stream after condensation in K3C1-N
160 return stream of K3
161 bottom product of K4
162 vapour stream of K4
163 return stream of K4
164 efflux of liquid from the lower stripping section of K3
166 residual vapour stream after condensation in K4C1-N
167 purge stream from the bottom product of K4
169 vapour stream from stripping section of K3 to the feed side (embodiment as a dividing wall column)

All references cited herein are hereby incorporated by reference for all useful purposes.

The examples which follow serve to illustrate the invention by way of example and should not be interpreted as a restriction.

EXAMPLES

The examples are intended to represent the process according to the invention with regard to the recycling of the ethylene glycol, obtained in the preparation of dimethyl carbonate, to give ethylene carbonate, and the reaction thereof with methanol to give dimethyl carbonate, which can be used in the diphenyl carbonate preparation process (DPC process) with phenol, with recycling of the phenol formed in the preparation of polycarbonate to the preparation of diphenyl carbonate (FIG. 1).

Example 1

1) Preparation of Ethylene Carbonate from Carbon Dioxide and Ethylene Oxide An upright tube of length 100 cm and diameter 3 cm, which has been provided with an oil heating jacket and with a gas inlet frit at the lower end, was charged with 700 parts by weight of ethylene carbonate which contained, in dissolved form, 1.3 parts by weight of zinc bromide and 2.5 parts by weight of potassium iodide as catalysts, and preheated to 120° C. At this temperature, 74 parts by weight of ethylene oxide and 82 parts by weight of carbon dioxide as a gas mixture were introduced uniformly through the bottom frit within 4 h. The gas mixture was substantially absorbed. After the introduction of gas had ended, the mixture was discharged into a flask and weighed. The increase in weight thus determinable by weighing was 146 parts by weight. Taking account of the transfer loss, this corresponds to an almost quantitative conversion of the ethylene oxide. The gas chromatography analysis of the end product showed that no by-products had been formed. Subsequently, at 18-22 mbar, 160 parts by weight of ethylene carbonate were distilled out of this mixture.

2) Transesterification of Ethylene Carbonate with Methanol to Give Dimethyl Carbonate and Ethylene Glycol In an apparatus arrangement according to FIG. 2, a countercurrent transesterification column (I) with stripping section and rectifying section was heated with application of a temperature gradient such that the bottom temperature was about 120° C. and the top temperature about 50° C. Via (I), 367 parts by weight per hour of ethylene carbonate were metered in. Via (8), 872 parts by weight per hour of a mixture of 80% by weight of methanol and 20% by weight of dimethyl carbonate were metered in. Into the lower part of the column, but above the stripping section, 270 parts by weight per hour of methanol were metered in via (3), and a further 130 parts by weight per hour of methanol via (15). In addition, 37 to 38 parts by weight per hour of recycled bottoms containing 4% by weight of catalyst (KOH) were metered into the top of (I) via (13), and 1.2 parts by weight per hour of fresh potassium hydroxide via (2). To the extent that these streams metered in were internal streams, they were taken from the apparatuses shown in FIG. 2. The methanol-containing streams metered in rose in vaporous form to the top of the column, counter to the liquid ethylene carbonate containing the catalyst flowing downward, with transesterification to give dimethyl carbonate and ethylene glycol. At the top of (I) 1380 parts by weight per hour of a mixture (7) of 60% by weight of methanol and 40% by weight of dimethyl carbonate were withdrawn, which were introduced to a tray column (11) in the middle and separated at a pressure of 10 bar into a mixture of about 80% by weight of methanol and 20% by weight of dimethyl carbonate, and 378 parts by weight per hour of dimethyl carbonate (4). Said 872 parts by weight per hour of the mixture (8) withdrawn in vaporous form were recycled to (I), while the remaining portion of (8) was separated further in the column (V); this afforded a dimethyl carbonate-containing top product which was recycled to (11), and 130 parts by weight per hour of bottom product (15) consisting essentially of methanol, which was recycled to (I). The bottom product (9) of (I), which consisted essentially of ethylene glycol, small amounts of low boilers (methanol and dimethyl carbonate), high boilers such as diethylene glycol and the catalyst, passed into a falling-film evaporator (III), from which 38 parts by weight per hour of low boilers (10) were recycled to (I). 375 parts by weight per hour of bottom product (11) passed into a further falling-film evaporator (IV), from which 75 parts by weight per hour of concentrated catalyst solution (12) were withdrawn from the bottom thereof, about half of which was recycled via (13) to (I), and the other half was metered into a thin-film evaporator with separating attachment (VIII). 302 parts by weight per hour of vapour phase (17) from (IV) were metered into the column (VII). In (VII), another 77 parts by weight per hour of low boilers (18) were removed, which were recycled to (I). From the upper part of (VII), 255 to 256 parts by weight of glycol (22) were withdrawn in a side draw, which, according to purity requirements, could be treated further in (IX) to give high-purity glycol (5) at a rate of 255 parts by weight per hour. The bottom efflux (19) of (VII) in an amount of 58 to 59 parts by weight per hour was supplied together with half of the bottom efflux (12) from (IV) to a thin-film evaporator (VIII), the distillate (21) of which was fed at a rate of 91 parts by weight per hour into the lower part of (VII). The concentrated bottoms (6) of (VIII) comprising all high boilers and a portion of the catalyst were sent to disposal.

3a) Oxidative Carbonylation of Ethylene Glycol with Carbon Monoxide and Oxygen to Give Ethylene Carbonate An autoclave of 20 parts by volume in size was charged with ethane-1,2-diol (80.33% by weight), $PdAc_2$ (0.23% by weight), $Mn(acac)_3$ (7.22% by weight), KBr (12.22% by weight) and DME (2 parts by volume). 20 bar of a gas mixture of nitrogen/oxygen/carbon monoxide (weight ratio 91:3:6) were injected and the reaction mixture was heated to 60° C. for 20 hours. After cooling, the reaction mixture was analysed by gas chromatography.

Ethylene carbonate was obtained in 20.3% yield. This corresponds to a TON in relation to palladium of 255, and to a TOF in relation to palladium of 12.8 $h^{-1}$. Ethylene carbonate was the only detectable product.

3b) Oxidative Carbonylation of Propylene Glycol with Carbon Monoxide and Oxygen to Give Propylene Carbonate An autoclave of 20 parts by volume in size was charged with propane-1,2-diol (83.35% by weight), $PdAc_2$ (0.19% by weight), $Mn(acac)_3$ (6.11% by weight), KBr (10.35% by weight) and DME (2 parts by volume). 20 bar of a gas mixture of nitrogen/oxygen/carbon monoxide (weight ratio 91:3:6) were injected and the reaction mixture was heated to 60° C. for 20 hours. After cooling, the reaction mixture was analysed by gas chromatography.

Propylene carbonate was obtained in 27.3% yield. This corresponds to a TON in relation to palladium of 342, and to a TOF in relation to palladium of 17.1 $h^{-1}$. Propylene carbonate was the only detectable product.

4) Preparation of Diphenyl Carbonate by Transesterification of Dimethyl Carbonate with Phenol In an apparatus arrangement according to FIG. 3, a first reaction column ($K_1$) comprising an upper rectifying section ($K_1VT_2$) with 4 theoretical plates, an intermediate condenser ($K_1IC_1$), a lower rectifying section ($K_1VT_1$) with 4 theoretical plates, a reaction zone ($K_1RZ$) with 30 reaction trays (holdup: 12 parts by volume), with 3 trays equipped with heating elements ($K_1E\_RZ_{1-3}$), and a stripping section $K_1AT$ with 6 trays (holdup: 12 parts by volume) was charged with 399.3 parts by weight/h of a mixture (118) of 85.4% by weight of phenol, 9.2% by weight of dimethyl carbonate, 3.2% by weight of diphenyl carbonate, 1.5% by weight of titanium tetraphenoxide, 0.3% by weight of anisole, 0.3% by weight of methyl phenyl carbonate and 0.1% by weight of methanol at the upper end of the reaction zone. At the lower end of the reaction zone ($K_1RZ$), 539.6 parts by weight/h of a vapour mixture (117), superheated by 5° C., of 98.8% by weight of dimethyl carbonate, 0.9% by weight of phenol, 0.2% by weight of anisole and 0.1% by weight of methanol are supplied.

This affords, at the bottom of the column, 452.4 parts by weight/h of a product mixture (106) of 49.8% by weight of phenol, 28.2% by weight of MPC, 12.3% by weight of DPC, 8.1% by weight of DMC, 0.2% by weight of anisole and 1.4% by weight of titanium tetraphenoxide.

$K_1$ is operated at a top pressure (above $K_1VT_2$) of 3.6 bar and a return ratio of 1.15. A temperature of 230° C. is established in the bottom of the column and, in the reaction zone ($K_1RZ$), a mean reaction temperature of 215° C. A bottom vaporizer $K_1E_1$ and three intermediate vaporizers ($K_1E\_RZ_{1-3}$) in the reaction zone are operated with steam at a vapour pressure of 35 bar, the bottom vaporizer ($K_1E_1$) used being a natural circulation vaporizer, and the intermediate vaporizers used being heating registers integrated onto the reaction trays. The entrance temperature into the intermediate condenser (above $K_1IC_1$) is 205° C., the exit temperature 193° C. and the cooling output 57 kW. The heating output required to vaporize the dimethyl carbonate-comprising stream (115) is 52 kW. The vaporization and superheating of the dimethyl carbonate are effected at a temperature of 135 to 152° C.

The bottom product (106) of the first reaction column ($K_1$) is fed to a second reaction column ($K_2$) comprising a rectifying section ($K_2VT$) with 10 theoretical plates and a stripping section ($K_2AT$) with 22 theoretical plates.

In addition, 81.9 parts by weight/h of a mixture (109) of 69.9% by weight of methyl phenyl carbonate, 28.3% by weight of phenol, 1.2% by weight of dimethyl carbonate, 0.5% by weight of diphenyl ether and 0.1% by weight of diphenyl carbonate from the diphenyl carbonate fine distillation ($K_3$) are metered in the region of the stripping section ($K_2AT$).

This affords, at the bottom of the second reaction column ($K_2$), 236.6 parts by weight/h of a product mixture (108) of 62.8% by weight of diphenyl carbonate, 24.2% by weight of methyl phenyl carbonate, 9.8% by weight of phenol, 0.4% by weight of DMC, 2.6% by weight of titanium tetraphenoxide and 0.2% by weight of diphenyl ether.

Additionally withdrawn are 238.2 parts by weight/h of liquid distillate (103) comprising 83.5% by weight of phenol, 15.5% by weight of dimethyl carbonate, 0.6% by weight of methyl phenyl carbonate, 0.3% by weight of anisole and 0.1% by weight of methanol.

The second reaction column ($K_2$) is operated at a top pressure (above $K_2VT$) of 1 bar and a return ratio of 0.65. The mixture effluxing from stripping section ($K_2AT$) has a temperature of 198° C. and is fed into a two-stage evaporation. The exit temperature downstream of the first evaporation stage ($K_2E_1$) is 209° C. and, downstream of the second vaporizer stage ($K_2E_2$), 230° C. The vaporizers used are a natural circulation evaporator in the first stage and a kettle-type evaporator in the second stage. Since the catalyst is nonvolatile, the reaction is limited to the stripping section, the column bottom and the vaporizers. Owing to the comparatively low temperatures in the stripping section (188-198° C.), the reaction takes place predominantly in the column bottom and the vaporizers.

The bottoms mixture (108) obtained in the second reaction column ($K_2$) containing 62.7/24.2/9.8/0.4/2.6/0.03% by weight of DPC/MPC/phenol/DMC/Ti(PhO)$_4$/salol and a total amount of 236.6 parts by weight/h is fed to a distillative workup for the purpose of isolating the diphenyl carbonate, removing very high boilers and catalyst and low-boiling compounds. This consists of a diphenyl carbonate fine distillation column $K_3$ and a diphenyl carbonate sidestream column $K_4$ worked up according to FIG. 4.

The diphenyl carbonate fine distillation column ($K_3$) consists of four sectors, an upper rectifying section ($K_3VT_1$) with 5 theoretical plates, a lower rectifying section ($K_3VT_2$) with 3 theoretical plates, an upper stripping section ($K_3AT_1$) with 16 theoretical plates and a lower stripping section ($K_3AT_2$) with 9 theoretical plates. The condensation of the vapours leaving at the top of the column in the top condenser ($K_3C_1$) and the partial evaporation of the liquid effluxing from the lower stripping section ($K_3AT_2$) in the vaporizer ($K_3E_1$) for the bottom product are each effected in one stage.

The diphenyl carbonate fine distillation column ($K_3$) is operated at a top pressure of 15 mbar and a return ratio of 0.7.

This affords, as the distillate (109), a stream containing 69.9/28.3/1.2/0.5% by weight of MPC/phenol/DMC/DPE. Below the upper rectifying section ($K_3VT_1$), 0.02 part by weight/h of liquid is withdrawn for the purpose of discharge of intermediate boilers in the sidestream (153). In addition, below the upper rectifying section ($K_3VT_1$), 201 parts by weight/h of a vaporous sidestream (157) containing 99.9% by weight of DPC are withdrawn. The bottom product (155) obtained is 20.6 parts by weight/h of a mixture containing 70/29.8/0.2% by weight of DPC/Ti(PhO)$_4$/salol.

The vaporous sidestream (157) is fed to a sidestream column ($K_4$). This possesses only a rectifying section ($K_4VT$) with 9 theoretical plates.

The sidestream column ($K_4$) is operated under identical pressure conditions to the DPC fine distillation column ($K_3$) and at a return ratio of 0.5.

The vapours (162) leaving at the top of the sidestream column ($K_4$) are condensed in a two-stage condensation in the condensers ($K_4C_{1-2}$), the heat of condensation being used either to raise steam or to heat other process sections of the DPC preparation.

This affords a distillate (151) containing 99.96% by weight of DPC and only 300 ppm of salol. The liquid (161) effluxing at the bottom of the sidestream column is fed to the diphenyl carbonate fine distillation column ($K_3$) above the lower stripping section ($K_3AT_2$).

5) Preparation of Polycarbonate from Bisphenol A and Diphenyl Carbonate

From a reservoir, 8.600 parts by weight/h of melt mixture consisting of 4.425 parts by weight/h of diphenyl carbonate, prepared as described in example 4, and 4.175 parts by weight/h of bisphenol A, with addition of 0.52 part by weight/h of the phenol adduct of tetraphenylphosphonium phenoxide comprising 65.5% tetraphenylphosphonium phenoxide/h dissolved in 4.5 parts by weight/h phenol/h, are pumped through a heat exchanger, heated to 190° C. and conducted through a delay column at 12 bar and 190° C. The mean residence time is 50 minutes.

The melt is then passed through a decompression valve into a separator at 200 mbar. The effluxing melt is heated again to 189° C. in a falling-film evaporator likewise at 200 mbar, and collected in a receiver. After a residence time of 20 minutes, the melt is pumped into the next three stages, which are constructed in the same way. The conditions in the 2nd/3rd/4th stage are 100/74/40 mbar, 218/251/276° C. and 20/10/10 minutes. The oligomer formed has a relative viscosity of 1.09. All vapours are conducted via pressure regulators into a column under reduced pressure, and discharged as condensates.

Thereafter, the oligomer is condensed in a downstream basket reactor at 278° C. and 3.0 mbar for a residence time of 45 minutes to give a higher molecular weight product. The relative viscosity is 1.195. The vapours are condensed.

The melt stream is passed into a further basket reactor and a gear pump is used to branch off a substream of 150 parts by weight/h thereof, to which is added 0.185 part by weight/h of a 5% aqueous phosphoric acid, and the mixture is stirred using a static mixer with a length-to-diameter ratio of 20 and passed back into the main melt stream. Directly after the recombination, the phosphoric acid in the entire melt stream is distributed homogeneously by means of a further static mixer.

The melt thus treated continues to be exposed to the process conditions in a further basket reactor at 284° C., 0.7 mbar and a mean residence time of 130 minutes, and is discharged and pelletized.

The vapours are condensed in the vacuum system and beyond it.

The polycarbonate obtained has the following characteristics: relative viscosity 1.201/phenolic OH 255 [ppm]/DPC 71 [ppm]/BPA 6 [ppm]/phenol 56 [ppm].

The phenol distilled off can be recycled back into the diphenyl carbonate preparation according to step (h), as described in Example 4.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A process for preparing at least one diaryl carbonate from at least one dialkyl carbonate and at least one aromatic hydroxyl compound, comprising
   (a) preparing alkylene carbonate by reaction of alkylene oxide with carbon dioxide,
   (b) reacting the alkylene carbonate formed in step (a) with at least one alkyl alcohol in the presence of a catalyst, and optionally organic solvent, to form at least one dialkyl carbonate and alkylene glycol,
   (c) removing and working up at least a portion of the at least one dialkyl carbonate formed in step (b),
   (d) removing and optionally purifying at least a portion of the alkylene glycol formed in step (b),
   (e) oxidatively carbonylating at least a portion of the alkylene glycol removed in step (d) with carbon monoxide to give the alkylene carbonate with formation of water,
   (f) removing and optionally purifying at least a portion of the alkylene carbonate formed in step (e), (g) recycling at least a portion of the alkylene carbonate prepared in step (f) into the preparation of dialkyl carbonate in step (b), (h) reacting at least a portion of the dialkyl carbonate prepared in step (c) with a monophenol to give the alkyl aryl carbonate and/or diaryl carbonate and alkyl alcohol; optionally recycling at least a portion of the alkyl alcohol formed in step (h) into step (b), (i) disproportionating at least a portion of the alkyl aryl carbonate prepared in step (h) to give the diaryl carbonate and dialkyl carbonate and optionally recycling at least a portion of the diaryl carbonate and/or dialkyl carbonate prepared in step (i) into step (b), (j) transesterifying at least a portion of the diaryl carbonate prepared in step (i) with a bisphenol to give a oligo-/polycarbonate and a monophenol; optionally recycling at least a portion of the monophenol formed in step (j) into step (h).

2. The process according to claim 1, wherein the oxidative carbonylation in step (e) uses a catalyst comprising at least one noble metal selected from palladium, rhodium, iridium and platinum in elemental form or as the ionic or nonionic compounds thereof and a cocatalyst comprising at least one compound selected from manganese compounds, cobalt compounds and copper compounds.

3. The process according to claim 2, wherein the catalyst comprises salts or organometallic compounds of palladium in the II oxidation state, rhodium in the I or III oxidation state, iridium in the I or III oxidation state or platinum in the II oxidation state.

4. The process according to claim 2, wherein the catalyst comprises palladium in elemental form or as an ionic or nonionic compound.

5. The process according to claim 2, wherein the cocatalyst comprises at least one compound selected from the group consisting of manganese compounds, cobalt compounds and copper compounds, in a weight ratio of catalyst compound to cocatalyst of 1:1 to 1:100.

6. The process according to claim 5, wherein the weight ratio of catalyst compound to cocatalyst is from 1:2 to 1:30.

7. The process according to any of claim 1, wherein the cyclic alkylene carbonates are of the formula (I):

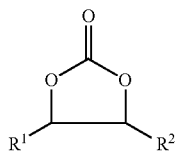

(I)

wherein, $R^1$ and $R^2$, independently of one another, represent hydrogen, substituted or unsubstituted $C_1$-$C_4$-alkyl, substituted or unsubstituted $C_2$-$C_4$-alkenyl or substituted or unsubstituted $C_6$-$C_{12}$-aryl and $R^1$ and $R^2$ together with the two five-membered ring carbon atoms may be a saturated carbocyclic ring having 5-8 ring members.

8. The process according to claim 7, wherein the cyclic alkylene carbonate is at least one compound selected from the group consisting of ethylene carbonate, propylene carbonate and butylene carbonate.

9. The process according to claim 1, wherein the dialkyl carbonates are of the formula (II):

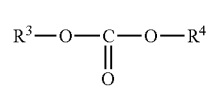

(II)

wherein $R^3$ and $R^4$, independently of one another, represent a linear or branched, optionally substituted $C_1$-$C_{34}$-alkyl.

10. The process according to claim 9, wherein the dialkyl carbonate is selected from the group consisting of dimethyl carbonate, diethyl carbonate, di(n-propyl)carbonate, di(isopropyl)carbonate, di(n-butyl)carbonate, di(sec-butyl)carbonate, di(tert-butyl)carbonate and dihexyl carbonate.

11. The process according to claim 1, wherein the diaryl carbonates used are those of the formula (VII):

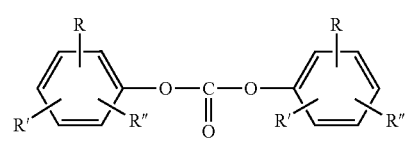

(VII)

wherein R, R' and R", independently of one another, represent H, linear or branched, optionally substituted $C_1$-$C_{34}$-alkyl, $C_1$-$C_{34}$-alkoxy, $C_5$-$C_{34}$-cycloalkyl, $C_7$-$C_{34}$-alkylaryl, $C_6$-$C_{34}$-aryl or a halogen radical; wherein R, R' and R" on both sides of the formula (VII) may be the same or different; and wherein R may also represent —COO—R'" where R'" represents H, optionally branched $C_1$-$C_{34}$-alkyl, $C_1$-$C_{34}$-alkoxy, $C_5$-$C_{34}$-cycloalkyl, $C_7$-$C_{34}$-alkylaryl or $C_6$-$C_{34}$-aryl.

12. The process according to claim 11, wherein the diaryl carbonate is selected from the group consisting of diphenyl carbonate, 4-tert-butylphenyl phenyl carbonate, di(4-tert-butylphenyl)carbonate, biphenyl-4-yl phenyl carbonate, di(biphenyl-4-yl)carbonate, 4-(1-methyl-1-phenyl ethyl)phenyl phenyl carbonate and di[4-(1-methyl-1-phenylethyl)phenyl] carbonate.

13. A polycarbonate obtained from the processes according to claim 1.

* * * * *